United States Patent
Daly et al.

(10) Patent No.: US 9,359,270 B2
(45) Date of Patent: Jun. 7, 2016

(54) TREATING OF CATALYST SUPPORT

(71) Applicant: Oxford Catalysts Limited, Abingdon, Oxfordshire (GB)

(72) Inventors: Frank Daly, Waldoboro, ME (US); Laura Richard, Abingdon (GB)

(73) Assignee: Velocys Technologies Limited, Abingdon, Oxfordshire (GB)

(*) Notice: Subject to any disclaimer, the term of this patent is extended or adjusted under 35 U.S.C. 154(b) by 379 days.

(21) Appl. No.: 13/961,166

(22) Filed: Aug. 7, 2013

(65) Prior Publication Data
US 2014/0045953 A1    Feb. 13, 2014

(30) Foreign Application Priority Data
Aug. 7, 2012 (GB) .................................. 1214122.2

(51) Int. Cl.
*B01J 21/04*    (2006.01)
*B01J 23/26*    (2006.01)
(Continued)

(52) U.S. Cl.
CPC . *C07C 1/043* (2013.01); *B01J 8/00* (2013.01); *B01J 19/0093* (2013.01); *B01J 21/08* (2013.01);
(Continued)

(58) Field of Classification Search
CPC ........ B01J 21/04; B01J 21/063; B01J 21/066; B01J 23/26; B01J 23/34; B01J 37/02; B01J 37/024; B01J 37/08; B01J 37/088; B01J 37/14; C10G 2/33; C10G 2/34
USPC ......... 502/305, 308, 319, 320, 324, 349–351, 502/355
See application file for complete search history.

(56) References Cited

U.S. PATENT DOCUMENTS 4,332,914 A * 6/1982 Knifton ................. C07C 29/157 502/161
4,537,909 A * 8/1985 Lin ....................... C07C 29/158 518/713

(Continued)

FOREIGN PATENT DOCUMENTS

EP    1 239 019 A1    9/2002
EP    1 359 237 A1    11/2003
(Continued)

OTHER PUBLICATIONS

Agnieszka Michalak et al.; "Physico-Chemical Properties of Cobalt-Ruthenium (10% Co-0.5% Ru) Catalysts Supported on Binary Oxides 8.5% ZrO$_2$/Support (SiO$_2$, Al$_2$O$_3$, TiO$_2$) for Fischer-Tropsch Synthesis", Topics in Catalysis, Kluwer Academic Publishers-Plenum Publishers, NE, vol. 52, No. 8, Apr. 14, 2009, pp. 1044-1050.
(Continued)

*Primary Examiner* — Patricia L Hailey
(74) *Attorney, Agent, or Firm* — Renner, Otto, Boisselle & Sklar, LLP

(57) ABSTRACT

A method for the preparation of a modified catalyst support comprising: (a) treating a catalyst support material with an aqueous solution or dispersion comprising one or more zirconium metal sources, chromium metal sources, manganese metal sources and aluminum metal sources, and one or more polar organic compounds; and (b) drying the treated support, and (c) optionally calcining the treated support. Also provided are catalyst support materials obtainable by the methods, and catalysts prepared from such supports.

45 Claims, 2 Drawing Sheets

(51) Int. Cl.

| | |
|---|---|
| B01J 37/02 | (2006.01) |
| B01J 37/08 | (2006.01) |
| B01J 37/14 | (2006.01) |
| C07C 1/04 | (2006.01) |
| B01J 23/89 | (2006.01) |
| B01J 37/18 | (2006.01) |
| B01J 19/00 | (2006.01) |
| B01J 8/00 | (2006.01) |
| B01J 35/00 | (2006.01) |
| B01J 35/10 | (2006.01) |
| C10G 2/00 | (2006.01) |
| B01J 21/08 | (2006.01) |
| B01J 23/34 | (2006.01) |
| B01J 37/16 | (2006.01) |

(52) U.S. Cl.
CPC ........... *B01J 23/26* (2013.01); *B01J 23/34* (2013.01); *B01J 23/8913* (2013.01); *B01J 23/8993* (2013.01); *B01J 35/006* (2013.01); *B01J 35/0046* (2013.01); *B01J 35/0053* (2013.01); *B01J 35/0066* (2013.01); *B01J 35/1014* (2013.01); *B01J 35/1019* (2013.01); *B01J 35/1038* (2013.01); *B01J 35/1042* (2013.01); *B01J 35/1061* (2013.01); *B01J 37/0203* (2013.01); *B01J 37/0205* (2013.01); *B01J 37/0207* (2013.01); *B01J 37/0213* (2013.01); *B01J 37/08* (2013.01); *B01J 37/088* (2013.01); *B01J 37/16* (2013.01); *B01J 37/18* (2013.01); *C10G 2/33* (2013.01); *C10G 2/333* (2013.01); *C10G 2/34* (2013.01); *B01J 23/8986* (2013.01); *B01J 2208/00796* (2013.01); *B01J 2219/00781* (2013.01); *B01J 2219/00835* (2013.01); *B01J 2219/00873* (2013.01)

(56) References Cited

U.S. PATENT DOCUMENTS

| | | | | |
|---|---|---|---|---|
| 4,622,343 | A * | 11/1986 | Knifton | C07C 29/157 502/155 |
| 5,397,806 | A | 3/1995 | Soled et al. | |
| 5,759,947 | A | 6/1998 | Zhou | |
| 5,958,985 | A * | 9/1999 | Geerlings | B01J 23/8892 502/324 |
| 6,013,313 | A * | 1/2000 | Nunan | B01J 37/0018 427/214 |
| 6,040,265 | A | 3/2000 | Nunan | |
| 6,362,239 | B1 * | 3/2002 | Buess | B01J 23/8892 518/713 |
| 6,576,584 | B1 * | 6/2003 | Iijima | B01J 23/882 502/202 |
| 7,510,994 | B2 | 3/2009 | Ikeda et al. | |
| 8,569,388 | B2 * | 10/2013 | Verhaak | B01J 23/8892 518/700 |
| 8,618,016 | B2 * | 12/2013 | Steiner | B01J 23/002 502/324 |
| 2005/0026776 | A1 | 2/2005 | Yamada et al. | |
| 2009/0293359 | A1 | 12/2009 | Simmons et al. | |
| 2009/0305881 | A1 | 12/2009 | Sietsma et al. | |
| 2010/0024874 | A1 | 2/2010 | Varaprasad | |
| 2010/0175588 | A1 | 7/2010 | Schorr et al. | |
| 2011/0028575 | A1 | 2/2011 | Van De Loosdrecht | |
| 2014/0088206 | A1 * | 3/2014 | Daly | B01J 21/063 518/715 |

FOREIGN PATENT DOCUMENTS

| | | |
|---|---|---|
| EP | 1 374 978 A1 | 1/2004 |
| JP | 5-184921 | 7/1993 |
| JP | 2004016975 | 1/2004 |
| JP | 2007252989 | 10/2007 |
| KR | 100759430 | 10/2007 |
| WO | WO 01/83108 A1 | 11/2001 |
| WO | WO 02/074431 A1 | 9/2002 |
| WO | WO 2006/012152 A2 | 2/2006 |
| WO | WO 2007/068731 A1 | 6/2007 |
| WO | WO 2008/104793 A2 | 9/2008 |
| WO | WO 2010/049715 A1 | 5/2010 |
| WO | WO 2010/097754 A2 | 9/2010 |
| WO | WO 2010/115105 A1 | 10/2010 |

OTHER PUBLICATIONS

Yi Zhang et al.; "A New Preparation Method of Bimodal Catalyst Support and its Application in Fischer-Tropsch Synthesis", Topics in Catalysis, Kluwer Academic Publishers-Plenum Publishers, NE, vol. 26, No. 1-4, Dec. 1, 2003, pp. 129-137.

Liu Y et al.; "Fischer-Tropsch synthesis in slurry-phase reactors over Mn- and Zr-modified Co/SiO$_2$ catalysts", Fuel Processing Technology, vol. 90, No. 7-8, Jul. 1, 2009, pp. 901-908.

Partial International Search Report for PCT/GB2013/052103.

Great Britain Search Report, Application No. GB1102101.1, dated Jun. 3, 2011.

Great Britain Further Search Report, Application No. GB1102101.1, dated Oct. 4, 2011.

Great Britain Search Report, Application No. GB1201619.2, dated May 28, 2012.

Kakihana et al.; "Application of Water-Soluble Titanium Complexes as Precursors for Synthesis of Titanium-Containing Oxides via Aqueous Solution Processes"; Bull. Chem. Soc. Jpn 2010, 83 (11), pp. 1285-1308.

Mohamed et al.; "Synthesis, characterization and catalytic properties of titania-silica catalysts"; Colloids and Surfaces, A: Physicochemical and Engineering Aspects 207 (2002) 25-32.

Riva et al.; "Metal-support interaction in Co/SiO$_2$ and Co/TiO$_2$"; Applied Catalysis A: General 196 (2000) 111-123.

Song et al.; "The role if impregnation medium on the activity of ceria-supported cobalt catalysts for ethanol steam reforming"; Journal of Molecular Catalysis A: Chemical 318 (2010) 21-29.

Hinchiranan et al.; "TiO$_2$ promoted Co/SiO$_2$ catalysts for Fischer-Tropsch synthesis"; Fuel Processing Technology 89 (2008), 455-459.

Bouh et al.; "Mono- and Dinuclear Silica-Supported Titanium (IV) Complexes and the Effect of TiOTi Connectivity on Reactivity"; J. Am. Chem. Soc. 1999, 121, 7201-7210.

Bu et al.; "Preparation and Characterization of TiO$_2$-Supported on the Surface of SiO$_2$"; Advanced Materials Research vols. 194-196 (2011) pp. 1807-1810.

Castillo et al.; "Influence of Preparation Methods on the Texture and Structure of Titania supported on Silica"; J. Mater. Chem. 1994, 4(6), 903-906.

U.S. Appl. No. 14/419,658, filed Feb. 5, 2015.

\* cited by examiner

TREATING OF CATALYST SUPPORT

This application claims priority to GB Patent Application No. 1214122.2 filed Aug. 7, 2012, which is hereby incorporated herein by reference in its entirety.

INTRODUCTORY PARAGRAPH

The present invention relates to a method for the preparation of a modified catalyst support and the catalyst supports formed using this method. The present invention also relates to catalyst precursors and catalysts formed on the modified catalyst support.

The supports, precursors and catalysts of the present invention are particularly suitable for use in Fischer-Tropsch reactions.

BACKGROUND

All documents cited herein are incorporated by reference in their entirety.

The modification of catalyst supports has conventionally been carried out using organic solvents, as described in, for example, Bouh et al., J. Am. Chem. Soc, 121 (1999) 7201, Bu et al., Advanced Materials Research, 194 (2011) 1807 and US patent application US 2010/0024874 A1. In the modern era, there is a continual push towards more environmentally friendly, or "greener", technologies. This push has caused considerable interest in water-based processes in the catalyst manufacturing industry. Furthermore, the use of aqueous methods, compared to non-aqueous methods, often results in a lowering of manufacturing costs.

Therefore, there is a need for further aqueous methods for the preparation of modified catalyst supports.

U.S. Pat. No. 7,510,994 discloses a method of loading an oxide of titanium onto a support in film form in an amount of from 0.5 to 10% through impregnation with an aqueous solution containing compounds which act as titanium sources.

Jeung et al., J. Chem. Soc. Faraday Trans., 91 (1995) 953 discloses modifying silica with chromium using a standard incipient wetness method. Oh et al., Powder Tech., 204 (2010) 154 discloses modifying silica with manganese using a standard incipient wetness method. Meijers et al., Applied Catalysis, 70 (1991) discloses impregnating a support with zirconium using an alkoxide method.

An object of the present invention is to provide an improved method for the preparation of a modified catalyst support.

A further object of the present invention is to provide improved modified catalyst supports, catalyst precursors and catalysts.

STATEMENT OF INVENTION

The present invention provides a method for the preparation of a modified catalyst support comprising (a) treating a catalyst support material with an aqueous solution or dispersion comprising a metal source and one or more polar organic compounds, wherein the metal source comprises one or more of a zirconium metal source, a chromium metal source, a manganese metal source and an aluminium metal source, and (b) drying the treated support and (c) optionally calcining the treated support.

The aqueous solution or dispersion in step (a) may comprise sources of two or more different metals. Preferably, although a first metal source is selected from a zirconium metal source, a chromium metal source, a manganese metal source and an aluminium metal source, the second or subsequent metal source may be selected from a zirconium metal source, a manganese metal source, a chromium metal source, an aluminium metal source and a titanium metal source as long as the metal in the second metal source is different to the metal in the first metal source. In this way, the catalyst support material may undergo simultaneous modification by at least two different metals.

In any of the methods described herein, there may be a further step (d) of treating the modified catalyst support with a further aqueous solution or dispersion comprising a metal source and one or more polar organic compounds, wherein the metal source comprises a different metal to the metal in the metal source comprised in step (a). Following step (d), there is subsequently a step (e) of drying the treated support and optionally a step (f) of calcining the treated support. Further steps (d) and (e) and optionally step (f) may be carried out either before step (a) or after step (b), or optionally after step (c), Preferably, the metal source in the aqueous solution or dispersion in step (d) comprises a zirconium metal source, a manganese metal source, a chromium metal source, an aluminium metal source or a titanium metal source. In this way, the catalyst support material may undergo sequential modification by at least two different metals.

The metal source used in step (a) may comprise one or both of a zirconium metal source and a chromium metal source.

Preferably, the metal source used in step (a) may comprise a zirconium metal source. The use of a zirconium metal source may provide a zirconium oxide-modified catalyst support that can be used to generate catalysts with particularly good CO conversion levels and which can thus function well as a Fischer-Tropsch catalyst. Catalysts based on zirconium oxide-modified catalyst supports are particularly advantageous because they have good $CH_4$ selectivity. Preferably, the zirconium metal source comprises zirconium dinitrate oxide hydrate.

One or more zirconium metal sources may be used in the aqueous solution or dispersion. The aqueous solution or dispersion may comprise one or more different metal sources in addition to the zirconium metal source, preferably one or more of a chromium metal source, manganese metal source, aluminium metal source or titanium metal source. Alternatively, or in addition, the method comprises step (d) wherein the aqueous solution or dispersion or step (d) comprises a chromium metal source, manganese metal source, aluminium metal source or titanium metal source and one or more polar organic compounds.

The metal source used in step (a) may comprise a chromium metal source. The use of a chromium metal source may provide a chromium oxide-modified catalyst support that can be used to generate catalysts with particularly good CO conversion levels and can thus function well as a Fischer-Tropsch catalyst. Preferably, the chromium metal source comprises chromium (III) nitrate nonahydrate.

One or more chromium metal sources may be used in the aqueous solution or dispersion. The aqueous solution or dispersion may comprise one or more different metal sources in addition to the chromium metal source, preferably one or more of a zirconium metal source, manganese metal source, aluminium metal source or titanium metal source. Alternatively, or in addition, the method comprises step (d) wherein the aqueous solution or dispersion or step (d) comprises a manganese metal source, zirconium metal source, aluminium metal source or titanium metal source and one or more polar organic compounds.

The one or more metal sources used in step (a) may comprise a manganese metal source. Preferably, the manganese metal source comprises manganese (II) nitrate tetrahydrate. One or more manganese metal sources may be used in the aqueous solution or dispersion. The aqueous solution or dispersion may comprise one or more different metal sources in addition to the manganese metal source, preferably one or more of a zirconium metal source, chromium metal source, aluminium metal source or titanium metal source. Alternatively, or in addition, the method comprises step (d) wherein the aqueous solution or dispersion or step (d) comprises a chromium metal source, zirconium metal source, aluminium metal source or titanium metal source and one or more polar organic compounds.

The one or more metal sources used in step (a) may comprise an aluminium metal source. Preferably, the aluminium metal source comprises aluminium nitrate. One or more aluminium metal sources may be used in the aqueous solution or dispersion. The aqueous solution or dispersion may comprise one or more different metal sources in addition to the aluminium metal source, preferably one or more of a zirconium metal source, chromium metal source, manganese metal source or titanium metal source. Alternatively, or in addition, the method comprises step (d) wherein the aqueous solution or dispersion of step (d) comprises a chromium metal source, zirconium metal source, manganese metal source or titanium metal source and one or more polar organic compounds. The aqueous solution or dispersion of step (d) may be as defined in the same way as the corresponding features of the aqueous solution or dispersion of step (a) described herein.

This method is advantageous for environmental reasons. In particular, aqueous methods are more environmentally friendly than non-aqueous methods because the by-products of aqueous methods are easier to dispose of safely and are less toxic.

This method is advantageous because it provides a modified catalyst support which, when used to manufacture a catalyst, provides a highly active catalyst as shown in the examples of this application.

The present invention also provides a modified catalyst support obtainable by the methods described herein.

The modified catalyst support of the present invention is advantageous because it yields a catalyst that is more stable than catalysts derived from alternative supports. This is also shown in the examples of this application.

The modified catalyst support of the present invention is advantageous because it can be used to manufacture a more active catalyst as shown in the examples of this application.

The present invention also provides a method for preparing a catalyst precursor comprising (a) depositing a solution or suspension comprising at least one catalyst metal precursor and a complexing/reducing agent onto the modified catalyst support according to the present invention; (b) optionally drying the modified catalyst support onto which the solution or suspension has been deposited; and (c) calcining the modified catalyst support onto which the solution or suspension has been deposited.

The present invention also provides a catalyst precursor obtainable by the method according to this aspect of the invention. The present invention further provides a catalyst precursor comprising the modified catalyst support according to the invention.

A catalyst precursor comprising the modified catalyst support of the present invention is advantageous because it is more stable than a catalyst precursor comprising a modified catalyst support synthesised by alternative methods. This is shown in the examples of this application.

A catalyst precursor comprising the modified support of the present invention is advantageous because it can be activated to provide a more active catalyst as shown in the examples of this application.

The present invention also provides a catalyst obtainable by activation of the catalyst precursor according to these aspects of the invention.

A catalyst comprising the modified catalyst support of the present invention is advantageous because it is a more active catalyst as shown in the examples of this application.

In addition, a catalyst comprising the modified catalyst support of the present invention is advantageous because it has a lower deactivation rate (i.e. is more stable) compared to catalysts comprising alternative modified catalyst supports. This is shown in the examples of this application.

The present invention also provides the use of the modified catalyst support according to the present invention as a substrate in the manufacture of a Fischer-Tropsch catalyst.

The present invention also provides the use of a catalyst comprising the modified catalyst support according to the present invention to catalyse a Fischer-Tropsch reaction.

The present invention also provides the use of the catalyst precursor according to the present invention to form a Fischer-Tropsch catalyst.

The present invention also provides a catalyst precursor comprising:
  (i) a modified catalyst support obtainable by the methods described herein; and
  (ii) $Co_3O_4$ on the catalyst support,
wherein the numerical average particle diameter of the $Co_3O_4$ is less than 12 nm as determined by X-ray diffraction (XRD).

Preferably, the c value of a lognormal particle size distribution of $Co_3O_4$ is less than or equal to 0.31. The c-value is known as "the dimensionless ratio".

Alternatively or in addition, the D-value of the lognormal particle size distribution of $Co_3O_4$ is greater than or equal to about 19.

The D-value is a reformulation of the size distribution as described by the c-value and does not represent any new data. Therefore, the c- and D-values are mathematically related. A D-value of 19.2 is equivalent to an average particle size of about 10 nm and a size distribution width of about 0.31. It is preferred to use the D-value as this number incorporates both the size and distribution width into a single metric.

The present invention also provides a catalyst precursor comprising:
  a modified catalyst support obtainable by the methods described herein comprising silica; and
  $Co_3O_4$ on the catalyst support, where the catalyst is in the form of a particulate catalyst with a particle size distribution of d10 greater than 90 μm and d90 less than 310 μm.

The present invention also provides a catalyst precursor comprising:
  a zirconium oxide-modified silica catalyst support obtainable by the methods described herein;
  at least 35 wt % Co at least partially in the form of $Co_3O_4$, wherein the numerical average particle diameter of the $Co_3O_4$ is 8 to 10 nm as determined by XRD; and
  optionally Pt as a promoter;
  optionally Re as a promoter;
  wherein one or more of the following conditions is satisfied:
    the mean particle size distribution of the support is between 180 and 300 μm;
    the mean pore volume is less than 1 ml/g; and the mean pore diameter is less than 250 Å, preferably from 100 to 250 Å, more preferably from 125 to 200 Å. The catalyst precursor may comprise at least 40 wt % Co at least partially in the form of $Co_3O_4$, wherein the numerical average particle diameter of the $Co_3O_4$ is 8 to 10 nm as determined by XRD. The catalyst precursor may comprise Pt as a promoter.

The present invention also provides a catalyst precursor comprising:
a chromium oxide-modified silica catalyst support obtainable by the methods described herein;
at least 35 wt % Co at least partially in the form of $Co_3O_4$, wherein the numerical average particle diameter of the $Co_3O_4$ is 8 to 10 nm as determined by XRD; and
optionally Pt as a promoter;
optionally Re as a promoter;
wherein one or more of the following conditions is satisfied
the mean particle size distribution of the support is between 180 and 300 μm;
the mean pore volume is less than 1 ml/g;
the mean pore diameter is less than 175 Å, preferably from 100 to 175 Å. The catalyst precursor may comprise at least 40 wt % Co at least partially in the form of $Co_3O_4$, wherein the numerical average particle diameter of the $Co_3O_4$ is 8 to 10 nm as determined by XRD. The catalyst precursor may comprise Pt as a promoter.

The present invention also provides a catalyst precursor comprising:
a manganese oxide-modified silica catalyst support obtainable by the methods described herein;
at least 35 wt % Co at least partially in the form of $Co_3O_4$, wherein the numerical average particle diameter of the $Co_3O_4$ is 8 to 10 nm as determined by XRD; and
optionally Pt as a promoter;
optionally Re as a promoter;
wherein one or more of the following conditions is satisfied:
the mean particle size distribution of the support is between 180 and 300 μm;
the mean pore volume is less than 1 ml/g; and
the mean pore diameter is less than 200 Å, preferably from 100 to 200 Å. The catalyst precursor may comprise at least 40 wt % Co at least partially in the form of $Co_3O_4$, wherein the numerical average particle diameter of the $Co_3O_4$ is 8 to 10 nm as determined by XRD. The catalyst precursor may comprise Pt as a promoter.

The present invention also provides the use of the activated catalyst according to the present invention to catalyse a Fischer-Tropsch reaction.

The present invention provides a method of conducting a Fischer Tropsch reaction comprising using a catalyst as described herein or using a catalyst derived from a catalyst precursor described herein in a microchannel reactor, in which the performance of the catalyst is substantially maintained over a reaction period of about 5000 hours or more without regeneration of the catalyst, such that the contact time is less than 500 milliseconds, the CO conversion is greater than 50% and the methane selectivity is less than 15%. Preferably, the reaction period is about 8000 hours or more. Preferably, the CO conversion is greater than 60%. Preferably, the methane selectivity is less than 10%.

The present invention provides a method of conducting a Fischer Tropsch reaction comprising using a catalyst as described herein or using a catalyst derived from a catalyst precursor as described herein in a microchannel reactor in a temperature range of from about 180° C. to about 230° C., in which the deactivation rate of the catalyst measured as percent loss of CO conversion per day is 0.09% or less over a reaction period of about 5000 hours or more. Preferably, the reaction period is about 8000 hours or more. Preferably, the deactivation rate of the catalyst measured as percent loss of CO conversion per day is 0.085% by day or less.

As used herein, the term "comprising" encompasses "including" as well as "consisting" and "consisting essentially of" e.g. a composition "comprising" X may consist exclusively of X or may include something additional e.g. X+Y.

Support Modification Method

As used herein, the term "modified catalyst support" means a catalyst support material whose structure and/or composition has been altered by the incorporation of a refractory solid oxide or mixture of solid oxides in at least a part of the volume of the support material. By "catalyst support" as used herein encompasses a catalyst support which is a "bare catalyst support", which refers to a catalyst support material that is substantially free of catalytic metals, i.e. platinum group metals, iron, nickel, copper or cobalt. A suitable catalyst support material is silica or refractory oxides, for example refractory oxides of Mg, Si, Ti, Zn, Al, Zr, Hf, Y or Ce or mixtures thereof. Alternatively, the catalyst support material may comprise or consist essentially of carbon, a zeolite, a boronitride or silicon carbide. If the catalyst support material is also a refractory solid oxide, the refractory solid oxide which modifies the structure or composition of the catalyst support material will suitably be different to the catalyst support material. A catalyst may then be affixed to the modified catalyst support.

As used herein, the term "treating" when referring to the treating of a catalyst support material with the aqueous treatment solution described herein means a method of including a modifying material on or in the catalyst support material. Treating includes such methods as impregnating, coating, brushing, spraying, rolling or spreading. Preferred methods of treating are impregnation, for example by mixing an impregnation solution and the catalyst support in order to reach the point or incipient wetness or by spraying.

Treating of the catalyst support material with the modifying material may involve spraying the catalyst support material into the aqueous treatment solution one or more times (e.g. 1, 2, 3, 4, 5, 6, 7, 8, 9, 10 or more times). Each spraying of the support material may last from about 5 minutes to about 1 hour, preferably from about 15 minutes to about 30 minutes. Typically spraying of the basic support material takes place at a temperature of 30° C. or less. The volume of the solution or dispersion taken up by the catalyst support in the process may suitably range from about 0.5 to about 2.50 ml per gram of support material.

The catalyst support material, may be in the form of a structured shape, pellets or a powder.

The refractory solid oxide which modifies the catalyst support material may comprise or consist of a zirconium metal oxide, a chromium metal oxide, a manganese metal oxide and/or an aluminium metal oxide. Preferably, the refractory solid oxide is zirconium metal oxide or chromium metal oxide.

The modified catalyst support may be a zirconium oxide-modified support. Preferably, a zirconium oxide-modified silica support.

The modified catalyst support may be a chromium oxide-modified support. Preferably, a chromium oxide-modified silica support.

The modified catalyst support may be a manganese oxide-modified support. Preferably, a manganese oxide-modified silica support.

The modified catalyst support may be an aluminium oxide-modified support. Preferably, an aluminium oxide-modified silica support.

As used herein, the "aqueous treatment solution" is the aqueous solution or dispersion comprising one or more zirconium, chromium, manganese and/or aluminium metal sources and one or more polar organic compounds as described in claim 1.

The aqueous treatment solution is an aqueous solution or dispersion comprising one or more zirconium, chromium, manganese and/or aluminium metal sources and one or more polar organic compounds, preferably carboxylic acids.

The aqueous treatment solution may be an aqueous solution or dispersion comprising one or more zirconium metal sources and one or more polar organic compounds, preferably carboxylic acids.

The aqueous treatment solution may be an aqueous solution or dispersion comprising one or more chromium metal sources and one or more polar organic compounds, preferably carboxylic acids.

The aqueous treatment solution may be an aqueous solution or dispersion comprising one or more manganese metal sources and one or more polar organic compounds, preferably carboxylic acids.

The aqueous treatment solution may be an aqueous solution or dispersion comprising one or more aluminium metal sources and one or more polar organic compounds, preferably carboxylic acids.

The term "aqueous" herein refers to solutions or suspensions of the reagents in a solvent or solvent mixture that is predominantly (i.e. more than 50%, suitably more than 80%, for example more than 95%, and most typically about 100%) water. The aqueous treatment solution may comprise from about 50% w/v to about 95% w/v water, from about 68% w/v to about 88% w/v water, from about 70% w/v to about 75% w/v water.

Suitably, the zirconium, chromium, manganese or aluminium metal source may be present as a water soluble zirconium, chromium, manganese or aluminium metal ion complex or water soluble compound, preferably a complex. The metal source may comprise one single source of one metal or more than one different source of the same metal. Alternatively, the metal source may comprise different metal types selected from zirconium, chromium, manganese, aluminium and titanium.

The term "water soluble" herein signifies a solubility in water of at least about 10 g/liter to form a solution that is stable against precipitation for at least about one hour.

Suitable zirconium metal sources include ammonium zirconium carbonate, zirconium acetate and zirconium nitrate, such as zirconium nitrate pentahydrate, anhydrous zirconyl nitrate and zirconyl nitrate hydrate. Suitably, the zirconium metal source is substantially or completely free of sulphur and/or halide, since these could react adversely with the substrate, catalytic metal and/or metal promoter. Likewise, the zirconium metal source is suitably substantially free of metals other than the zirconium metal (e.g. sodium or potassium counter-ions) since these could react adversely with the substrate, catalytic metal and/or metal promoter. The zirconium metal source is preferably zirconyl nitrate, preferably zirconyl nitrate hydrate (also known as "zirconium dinitrate oxide hydrate").

The one or more zirconium metal sources may be present in the aqueous treatment solution in an amount (defined in terms of the weight of zirconium metal per volume of solution) of from about 1% w Zr/v to about 22% w Zr/v, preferably about 10% w Zr/v to about 20% w Zr/v.

Suitable chromium metal sources include chromium formate, chromium acetate, chromium nitrate such as anhydrous chromium nitrate and chromium nitrate nonahydrate. Suitably, the chromium metal source is substantially or completely free of sulphur and/or halide, since these could react adversely with the substrate, catalytic metal and/or metal promoter. Likewise, the chromium metal source is suitably substantially free of metals other than the chromium metal (e.g. sodium or potassium counter-ions) since these could react adversely with the substrate, catalytic metal and/or metal promoter. The chromium metal source is preferably a chromium nitrate, preferably chromium (III) nitrate nonahydrate.

The one or more chromium metal sources may be present in the aqueous treatment solution in an amount (defined in terms of the weight of chromium metal per volume of solution) of about 2% w Cr/v to about 15% w Cr/v, preferably about 5% w Cr/v to about 11% w Cr/v.

Suitable manganese metal sources include manganese acetate, manganese nitrate, such as manganese nitrate hexahydrate and manganese nitrate tetrahydrate. Suitably, the manganese metal source is substantially or completely free of sulphur and/or halide, since these could react adversely with the substrate, catalytic metal and/or metal promoter. Likewise, the soluble manganese metal source is suitably substantially free of metals other than the manganese metal (e.g. sodium or potassium counter-ions) since these could react adversely with the substrate, catalytic metal and/or metal promoter. The manganese metal source is preferably a manganese nitrate, preferably manganese (II) nitrate tetrahydrate.

The one or more manganese metal sources may be present in the aqueous treatment solution in an amount (defined in terms of the weight of manganese metal per volume of solution) of about 2% w Mn/v to about 15% w Mn/v, preferably about 5% w Mn/v to about 12% w Mn/v.

Suitable aluminium metal sources include aluminium nitrate, aluminium nitrate nonahydrate, aluminium lactate, aluminium acetate. Suitably, the aluminium metal source is substantially or completely free of sulphur and/or halide, since these could react adversely with the substrate, catalytic metal and/or metal promoter. Likewise, the aluminium metal source is suitably substantially free of metals other than the aluminium metal (e.g. sodium or potassium counter-ions) since these could react adversely with the substrate, catalytic metal and/or metal promoter.

The one or more aluminium metal sources may be present in the aqueous treatment solution in an amount (defined in terms of the weight of aluminium metal per volume of solution) of about 1% w Al/v to about 12% w Al/v, preferably about 3% w Al/v to about 6% w Al/v.

One or more polar organic compounds are present in the aqueous treatment solution.

The polar organic compound is preferably liquid at room temperature (20° C.). However, it is also possible to use polar organic compounds which become liquid at temperatures above room temperature. In such cases, the polar organic compound should preferably be liquid at a temperature below the temperature at which any of the components of the solution or dispersion decompose.

Examples of suitable organic compounds for inclusion in the solution or dispersion are organic amines, organic carboxylic acids, alcohols, phenoxides, in particular ammonium phenoxides, alkoxides, in particular ammonium alkoxides, amino acids, compounds containing functional groups such as one or more hydroxyl, amine, amide, carboxylic acid, ester, aldehyde, ketone, imine or imide groups, such as urea, hydroxyamines, trimethylamine, triethylamine, and surfactants.

Preferred alcohols are those containing from 1 to 30 carbon atoms, preferably 1 to 15 carbon atoms. Examples of suitable alcohols include methanol, ethanol and glycol and sugar alcohols, such as sorbitol.

Preferably, the polar organic compound is a carboxylic acid. The carboxylic acids are organic acids that are soluble in water.

Suitable carboxylic acids may be branched, linear or unbranched, saturated, unsaturated, aliphatic and/or aromatic, and/or derivatives thereof. Suitably, the carboxylic acid comprises or consists essentially of one or more dicarboxylic or tricarboxylic acids. Alternatively or in addition, the carboxylic acid may comprise one or more alpha- or beta-hydroxyl carboxylic acids. Examples of suitable carboxylic acids include acetic acid, citric acid, tartaric acid, malic acid, maleic acid, lactic acid, glycolic acid, propionic acid, succinic acid, oxalic acid and combinations thereof.

Mixtures or one of more different carboxylic acids may be used. In one embodiment, the mixture of one or more different carboxylic acids includes a tricarboxylic acid, preferably citric acid. In an alternative embodiment, the mixture of one or more different carboxylic acids includes an alpha hydroxyl carboxylic acid, such as lactic acid. In a further alternative embodiment, the mixture of one or more different carboxylic acids includes a tricarboxylic acid, preferably citric acid, and an alpha hydroxyl carboxylic acid, preferably lactic acid.

Preferred carboxylic acids are acetic acid, lactic acid, citric acid and mixtures thereof. More preferably, citric acid is present in the aqueous treatment solution.

Without wishing to be bound by theory, the inventors believe that the one or more carboxylic acids, particularly citric acid, in the aqueous treatment solution act as ligands to the zirconium, chromium, manganese or aluminium metal source thereby changing the coordination sphere around the metal. The carboxylic acid is also thought to replace OH groups on the catalyst support material (e.g. silica) forming dimeric and oligomeric zirconium, chromium, manganese or aluminium metal species on the surface of the catalyst support material leading to a higher dispersion of the metal species over the catalyst support material surface. This is thought to lead to the increased stability of a catalyst manufactured with the modified catalyst support.

The one or more carboxylic acids may be present in the aqueous treatment solution in an amount of about 1% w/v to about 30% w/v, preferably 2% w/v to about 25% w/v, preferably about 4% w/v to about 24% w/v, preferably about 5% w/v to about 20% w/v, preferably from about 18% w/v to about 20% w/v, more preferably from about 18% w/v to about 19% w/v.

Preferably, the aqueous treatment solution consists of a metal source precursor, a carboxylic acid and water, wherein the metal source precursor is selected from a zirconium, chromium, aluminium and manganese precursor.

A particularly preferred aqueous treatment solution for preparing a zirconium oxide-modified catalyst support has from about 10% w Zr/v to about 20% w Zr/v, from about 15% w/v to about 27% w/v of citric acid, preferably 18% w/v to about 20% w/v of citric acid.

A particularly preferred aqueous treatment solution for preparing a chromium oxide-modified catalyst support has from about 5% w Cr/v to about 11% w Cr/v, from about 12% w/v to about 25% w/v of citric acid, preferably from about 18% w/v to about 20% w/v of citric acid.

A particularly preferred aqueous treatment solution for preparing a manganese oxide-modified catalyst support has from about 5% w Mn/v to about 12% w Mn/v, from about 12% w/v to about 25% w/v of citric acid, preferably from about 18% w/v to about 20% w/v of citric acid.

A particularly preferred aqueous treatment solution for preparing an aluminium oxide-modified catalyst support has from about 3% w Al/v to about 6% w Al/v, from about 12% w/v to about 25% w/v of citric acid, preferably from about 18% w/v to about 20% w/v of citric acid.

The treated support is dried and optionally calcined following treatment. The purpose of the drying step and optional calcining step includes driving off water, which has an effect of increasing the support pore volume as compared to the just-impregnated state. Additionally, the metal oxide precursor and the polar organic compound may be partially decomposed during the heat treatment (although ideally not fully converted to the metal oxide). Without wishing to be bound by theory, the inventors feel that the presence of residual organic species on the catalyst support assists in the later dispersion of cobalt and thus may help improve the stability of the resulting catalyst.

One way of measuring the amount of residual organic species on the modified support is by determining the weight of the modified support after the drying and optional calcining steps and comparing this to the nominal weight of the support after full conversion to the metal oxide and removal of all water and precursor and polar organic compound species. The weight after drying/calcining should be higher than the nominal fully oxidised weight, indicating the presence of some additional species (presumed residual organic moieties). Suitable ranges for the weight ratio (weight after drying/calcining:nominal fully oxidised weight) may be 1.01 to 1.50, preferably 1.05 to 1.30, more preferably 1.10 to 1.25.

A suitable temperature for the drying step and optional calcining step is determined by identifying the temperature of decomposition of the metal oxide precursor plus polar organic compound mixture and selecting a temperature less than this. Suitably, the drying step and optional calcining step are carried out at a temperature from 100 to 350° C., from 150 to 300° C., or from 225 to 275° C.

The drying step may take place in a box furnace or muffle furnace. For example, where a box furnace or muffle furnace is used, drying may take place by heating at a temperature that increases at a rate (known as a "ramp rate") of 2° C./min up to a temperature of 100° C. and the temperature is then held at 100° C. for about 5 hours. Alternatively, drying may take place in other equipment, such as in a cone blender or in a rotary calciner. Where a rotary calciner is used, preferably the ramp rate is higher than 2° C./min and the holding time is shorter than 5 hours.

The treated support may be calcined following treatment. Calcining may further increase stability of a catalyst manufactured with the modified catalyst support. Calcination may use a programmed heating regime which increases the temperature gradually so as to control gas and heat generation from the treated support and the other components of the treatment solution. Suitably, calcination is carried out at a temperature from 100 to 350° C., preferably from 150 to 300° C., more preferably from 225 to 275° C. A preferred heating regime has a final temperature of up to 250° C. Preferably, the temperature ramp rate is 2° C./min. The final temperature should not exceed about 350° C. because calcining at higher temperatures reduces the amount of carbon and nitrogen retained on the modified support after drying and calcination, which has the effect of reducing catalyst stability. During calcination of the treated support, the final temperature is preferably held for about 5 hours.

The modified catalyst support of the present invention is preferably a modified Fischer-Tropsch catalyst support.
Modified Catalyst Support The present invention further provides a catalyst support obtainable by the method of the present invention.
Method of Preparation of Catalyst Precursor A method for preparing a catalyst precursor may comprise (a) depositing a solution or suspension comprising at least one catalyst metal precursor and a complexing/reducing agent onto the modified catalyst support of the present invention; (b) optionally drying the modified catalyst support onto which the solution or suspension has been deposited; and (c) calcining the modified catalyst support onto which the solution or suspension has been deposited.

Other methods for the preparation of catalyst precursors may be found in WO 2008/104793.

The catalyst metal precursor may be a cobalt-containing precursor or an iron-containing precursor. In one embodiment, the catalyst metal precursor is a cobalt-containing precursor.

Suitable cobalt-containing precursors include cobalt benzoylacetonate, cobalt carbonate, cobalt cyanide, cobalt hydroxide, cobalt oxalate, cobalt oxide, cobalt nitrate, cobalt acetate, cobalt acetylacetonate and cobalt citrate. These cobalt precursors can be used individually or in combination. These cobalt precursors may be in the form of hydrates or in anhydrous form. In some cases, where the cobalt precursor is not soluble in water, such as cobalt carbonate or cobalt hydroxide, a small amount of nitric acid or a carboxylic acid may be added to enable the precursor to fully dissolve in an aqueous solution or suspension.

The catalyst metal precursor may be cobalt nitrate. Cobalt nitrate may react with a complexing/reducing agent, such as citric acid, during calcination to produce $Co_3O_4$. The citric acid may act as a complexing/reducing agent and/or as a fuel (i.e. reducing agent for cobalt nitrate) in the calcination reaction.

Preferably, the catalyst precursor comprises cobalt on the modified catalyst support. More preferably, the catalyst precursor comprises $Co_3O_4$ on the modified catalyst support.

Without wishing to be bound by theory, the inventors believe that the activity and the selectivity of cobalt-based catalysts are principally influenced by the density of active sites, favouring very small particle sizes. However, the deactivation mechanisms of cobalt catalysts follow in general the reverse trend, where the largest particles are the most stable.

The inventors have found that a numerical average particle diameter of $Co_3O_4$ of less than 12 nm (determined by powder X-ray diffraction, preferably using a Siemens D5000 theta/theta powder diffractometer and Cu $K_\alpha$ radiation) gives a catalyst having optimum Fischer-Tropsch synthesis performance. The inventors have further found that the cobalt oxide particle size distribution influences the catalyst's activity and stability, such that, a particle size distribution as narrow as possible is preferred. The width of the particle size distribution can be measured by the c value of the lognormal particle size distribution. Preferably, the c value of the lognormal particle size distribution of $Co_3O_4$ particles is less than 0.31. The average particle diameter of $Co_3O_4$ may be below 11 nm, or between 8 and 10 nm. The c value may be between 0.19 and 0.31, or below 0.25, or between 0.19 and 0.25. Preferably, where the numerical average particle diameter of the $Co_3O_4$ is in the range 8 to 10 nm, c is less than 0.31.

Preferably, where the numerical average particle diameter is in the range 8 to 10 nm, the c-value may be 0.31 or less, e.g. 0.29 or less, 0.26 or less or 0.25 or less. Alternatively or in addition, the c-value may be 0.19 or more, e.g. 0.20 or more or 0.235 or more. It is within the scope of the present application to combine any of these upper and lower limits such that the c-value may be $0.19 \leq c \leq 0.31$; $0.19 \leq c \leq 0.29$; $0.19 \leq c \leq 0.26$; $0.19 \leq c \leq 0.25$; $0.20 \leq c \leq 0.31$; $0.20 \leq c \leq 0.29$; $0.20 \leq c \leq 0.26$; $0.20 \leq c \leq 0.25$; $0.235 \leq c \leq 0.31$; $0.235 \leq c \leq 0.29$; $0.235 \leq c \leq 0.26$; or $0.235 \leq c \leq 0.25$.

c is known as the dimensionless ratio, and characterises the width of the size distribution. In a sample of calcined catalyst (assuming spherical particles equivalent to crystallites or crystallites with a lognormal monomodal distribution) the form of the particle size distribution may be written as:

$$f(R) = \frac{1}{R\sqrt{2\pi \ln(1+c)}} e^{-\frac{\left[\ln\left(\frac{R}{R_O}\sqrt{1+c}\right)\right]^2}{2\ln(1+c)}} \text{ where } c = \frac{\sigma^2}{R_O^2} \quad \text{Equation 1}$$

where $R_O$ is the numeric average particle radius and c, which is known as the dimensionless ratio, characterises the width of the size distribution. Multiplication of $R_O$ by 2 yields the numerical average particle diameter.

An alternative way to characterise the relationship between the $Co_3O_4$ particle size distribution and the catalyst's activity and stability is through the D-value. It is important to note that the D-value is simply a reformulation of the size distribution as described by the c-value and does not represent any new data. Therefore, the c- and D-values are mathematically related, but an improved correlation is seen between the D-value and the catalyst's activity and stability.

The D-value is calculated from parameters of the particle size distribution of $Co_3O_4$ particles in a fresh, unreduced catalyst, i.e. in a catalyst precursor Trends between the c-value and the deactivation rate can be seen for $Co_3O_4$ particles of substantially the same numerical average particle diameter. The D-value is an improvement on the c-value because, while it still takes into account both the width of the $Co_3O_4$ particle size distribution and the numerical average particle diameter, it places a larger weighting on the numerical average $Co_3O_4$ particle diameter, which removes the need to maintain substantially the same numerical average particle diameter in order to observe trends in the data. This enables a single metric (D-value) to be reported and compared, rather than two metrics (c-value and numerical average particle diameter).

The D-value may be calculated by plotting the lognormal particle size distribution using Equation 1. The frequency at the mode of this lognormal distribution ($f_{mode}$) may be considered to be a measure of the width of the distribution. In order to account for the dependence of the FTS catalyst stability on numerical average particle diameter, the inventors have developed a formula in which $f_{mode}$ weighted by the size distribution median to create a "size-weighted distributed breadth", or D-value, using the formula:

$$D = f_{mode}{}^y \times R_O \times 2 \quad \text{Equation 2}$$

wherein $f_{mode}$ is the frequency at the mode of the lognormal distribution, $R_O$ is the numeric average particle radius, and y is an empirical value based on experimental observation. The value of y is determined via comparison of the stability of a selection of catalysts (at least about 5 to 10) with substantially similar compositions but small variations in $Co_3O_4$ particle size and size distribution width. These variations may be achieved via minor modifications of the synthesis method eg. increasing the dilution of the impregnation solution (which is shown in an example to cause subtle changes to the particle size distribution). FTS stability data on these catalysts under the same testing conditions is then collected. Within this set of similar catalysts, y is then manually adjusted to create a spread of D-values such that the difference in the stability of the FTS catalysts can be distinguished.

Therefore, an increase in the D-value represents either a narrowing of the particle size distribution or an increase in the numerical average particle diameter.

The inventors have further found that the $Co_3O_4$ particle size distribution influences catalyst's FTS activity and stability, such that, preferably, the D-value of the lognormal particle size distribution of $Co_3O_4$ particles is about 19 or more. A D-value of 19.2 corresponds to a size distribution with a c-value of about 0.31 and numerical average particle diameter of about 10 nm. A D-value of 19.8 corresponds to a size distribution with a c-value of about 0.31 and an average particle size of about 8 nm. In either of these cases, a decrease in c (eg. narrowing of the size distribution) would result in an increase in D. Therefore the specification of c≤0.31 over the average particle size range 8-10 nm corresponds to particle distributions defined by having D-values greater than or equal to about 19.

The D-value may be about 19 or more, e.g. 19.2 or more, 20.4 or more, 21.0 or more or 21.35 or more, or 21.4 or more. Alternatively or in addition, the D-value may be 23.5 or less, e.g. 22.2 or less. It is within the scope of the present application to combine any of these upper and lower limits such that the D-value may be 19≤D≤23.5; 19≤D≤22.2; 19.2≤D≤23.5; 19.2≤D≤22.2; 20.4≤D≤23.5; 20.4≤D≤22.2; 21.0≤D≤23.5; 21.0≤Dc≤22.2; 21.35≤D≤23.5; or 21.35≤D≤22.2.

The solution or suspension used in the method for preparing a catalyst precursor may contain a mixture of the primary catalyst metal precursor (i.e. a cobalt-containing precursors or an iron-containing precursor) and at least one secondary catalyst metal precursor. Such secondary catalyst metal precursor(s) may be present to provide a promoter and/or modifier in the catalyst. Suitable secondary catalyst metals include noble metals, such as Pd, Pt, Rh, Ru, Ir, Au, Ag and Os, transition metals, such as Zr, Ti, V, Cr, Mn, Fe, Co, Ni, Cu, Zn, Nb, Mo, Tc, Cd, Hf, Ta, W, Re, Hg and Ti and the 4f-block lanthanides, such as La, Ce, Pr, Nd, Pm, Sm, Eu, Gd, Tb, Dy, Ho, Er, Tm, Yb and Lu.

In particular, the secondary catalyst metals may be one or more of Pd, Pt, Ru, Ni, Co (if not the primary catalyst metal), Fe (if not the primary catalyst metal), Cu, Mn, Mo, Re and W.

Suitable complexing/reducing agents for use in the method of making the catalyst precursor of the present invention are the polar organic compounds as hereinbefore described. Preferred complexing/reducing agents are urea, carboxylic acids such as acetic acid, citric acid, glycolic acid, malic acid, propionic acid, succinic acid, lactic acid and oxalic acid. Mixtures of complexing/reducing agents may also be used.

If a catalyst metal precursor which is a hydrate is used, the solution or suspension will necessarily contain some water of hydration. This water may be sufficient to dissolve some of the components of the solution or suspension, such as the complexing/reducing agent (if solid at room temperature). However, in some cases, it may be necessary to add some water to the solution or suspension in order to ensure that the catalyst metal precursor(s) and the other components are able to dissolve or become suspended. In such cases, the amount of water used is usually the minimum required to allow the catalyst metal precursor(s) and the other components to dissolve or be suspended.

As will be clear to the skilled person, the choice of complexing/reducing agent will be partly dictated by the aqueous/non-aqueous nature of the solution or suspension. For example, if the solution or suspension is aqueous, a citric acid complexing/reducing agent is preferred because it provides a highly stable catalyst compared to other organic complexing/reducing agents such as polyols and sugars. The use of citric acid is also preferred because it provides a catalyst which is selective and stable at CO conversion levels greater than 70%.

The use of an aqueous method for the preparation of a modified catalyst support in combination with an aqueous method for the preparation of the catalyst precursor is advantageous for environmental reasons. In particular, aqueous methods are more environmentally friendly than non-aqueous methods because the by-products of aqueous methods are easier to dispose of safely and are less toxic. For example, most organic solvents are highly flammable and have low boiling points. As such, the vapours of these organic solvents tend to escape through the exhaust without decomposing. An effect of this is that manufacturing plants need to have extra safety measures in addition to COx and NOx scrubbers.

Optionally, the modified catalyst support onto which the solution or suspension has been deposited may be dried. Drying may take place at a temperature in the range from about 100° C. to about 130° C., preferably from about 100° C. to about 120° C. Drying may take place in a box oven, furnace or rotary calciner. Preferably drying takes place by heating at a temperature that increases at a ramp rate of 2° C./min up to a temperature of 100° C. and the temperature is then held at 100° C. for about 5 hours.

The modified catalyst support onto which the solution or suspension has been deposited may be calcined at a temperature in the range from about 200° C. to about 350° C., preferably from about 200° C. to about 250° C. Calcining may take place in a box oven, furnace or rotary calciner. Preferably, calcining takes place by heating at a temperature that increases at a ramp rate of 2° C./min up to a final temperature of 250° C. The temperature is held at 250° C. for about 3 hours. Alternatively, calcining preferably takes place by heating at a temperature that increases at a ramp rate of 2° C./min up to a temperature of 200° C. The temperature is held at 200° C. for about 3 hours before being increased again at a ramp rate of 1° C./min up to a temperature of 250° C. and then held at that temperature for a further 3 hours. The final temperature should not exceed about 250° C. because calcining at higher temperatures reduces the amount of carbon and nitrogen retained on the modified support after drying and calcination, which has the effect of reducing catalyst stability.

The deposition, drying and calcination steps may be repeated one or more times. For each repeat, the solution or suspension used in the deposition step may be the same or different. If the solution or suspension in each repetition is the same, the repetition of the steps allows the amount of catalyst metal(s) to be brought up to the desired level on the modified catalyst support stepwise in each repetition. If the solution or suspension in each repetition is different, the repetition of the steps allows schemes for bringing the amounts of different catalyst metals up to the desired level in a series of steps to be executed.

A programmed heating regime may be used during drying and calcination which increases the temperature gradually so as to control gas and heat generation from the catalyst metal precursors and the other components of the solution or suspension.

During the heating processes, the catalyst support may reach a maximum temperature of no more than 500° C., or no more than 375° C., or no more than 250° C. at atmospheric pressure.

The temperature may be ramped up at a rate of from 0.0001 to 10° C. per minute, or from 0.1 to 5° C. per minute.

An illustrative programmed heating regime may comprise:
(a) heating the catalyst support onto which the solution or suspension has been deposited at a rate of 1 to 10, or about 1 to 5, or about 2° C. per minute to a temperature of 80 to 120° C., or about 100° C. and maintaining it at this temperature for 0.25 to 10, or about 1 to 10, or about 5 hours;
(b) heating it at a rate of 1 to 10, or about 1 to 5, or about 2° C. per minute to a temperature of 150 to 400° C., or 200 to 350° C., or about 250° C. and maintaining it at this temperature for 0.25 to 6, or about 1 to 6, or about 3 hours.

The heating steps can be carried out in a rotating kiln, in a static oven or in a fluidised bed. Preferably, the heating steps are carried out in a rotating kiln because generally this has a more even temperature profile than a static oven.

Once the calcination step has been completed, either after the steps are first carried out or at the end of a repetition, further catalyst metals may optionally be loaded onto the catalyst support.

The calcination step may be carried out in an oxygen-containing atmosphere (e.g. air), in particular if metal catalyst oxides are to be formed.

Catalyst Precursor

A catalyst precursor is a material that may be activated to form a catalyst. The terms "catalyst" and "catalyst precursor" are used herein interchangeably and will be understood accordingly to their specific context.

A catalyst precursor comprises at least one catalyst metal, such as cobalt or iron, which may be present in oxide form, as elemental metal or as a mixture of any of these. In particular, the catalyst precursor may comprise from 10 to 60% cobalt and/or iron (based on the weight of the metal as a percentage of the total weight of the catalyst precursor), or from 35 to 50% of cobalt and/or iron, or from 40 to 44% of cobalt and/or iron or about 42% of cobalt and/or iron. The catalyst precursor may comprise both cobalt and iron, or it may not comprise iron. The cobalt may be present as $CO_3O_4$.

The catalyst precursor may comprise a noble metal on the support that may be one or more of Pd, Pt, Rh, Re, Ru, Ir, Au, Ag and Os. In particular, the noble metal may be selected from the group consisting of Ru, Re or Pt, and most suitably it comprises Pt. The catalyst precursor may suitably comprise from about 0.01 to about 1% in total of noble metal(s) (based on the total weight of all noble metals present as a percentage of the total weight of the catalyst precursor), or from about 0.015 to about 0.5% in total of noble metal(s), or from about 0.02 to about 0.3% in total of noble metal(s).

If desired, the catalyst precursor may include one or more other metal-based components as promoters or modifiers. These metal-based components may also be present in the catalyst precursor at least partially as oxides or elemental metals. A suitable metal for the one or more other metal-based components is one or more of Zr, Ti, V, Cr, Mn, Ni, Cu, Zn, Nb, Mo, Tc, Cd, Hf, Ta, W, Re, Hg, Tl and the 4f-block lanthanides. Suitable 4f-block lanthanides are La, Ce, Pr, Nd, Pm, Sm, Eu, Gd, Tb, Dy, Ho, Er, Tm, Yb and Lu. In particular, the metal for the one or more other metal-based components may be one or more of Zn, Cu, Mn, Mo and W. Alternatively, the metal for the one or more other metal-based components may be one or more of Re and Pt. The catalyst precursor may comprise from 0.01 to 10% in total of other metal(s) (based on the total weight of all the other metals as a percentage of the total weight of the catalyst precursor), or from 0.1 to 5% in total of other metals, or about 3% in total of other metals.

The catalyst precursor may contain up to 10% carbon (based on the weight of the carbon, in whatever form, in the catalyst as percentage of the total weight of the catalyst precursor), or from 0.001 to 5% of carbon, or about 0.01% of carbon. Alternatively, the catalyst precursor may comprise no carbon.

Optionally, the catalyst precursor may contain a nitrogen-containing organic compound such as urea, or an organic ligand such as an amine or a carboxylic acid, such as citric acid or acetic acid, which may be in the form of a salt or an ester.

The precursor may be activated to produce a Fischer-Tropsch catalyst, for instance by heating the catalyst precursor in hydrogen and/or a hydrocarbon gas, or in a hydrogen gas diluted with another gas, such as nitrogen and/or methane, to convert at least some of the oxides to elemental metal. In the active catalyst, the cobalt or iron may optionally be at least partially in the form of its oxide.

Catalyst Activation

The catalyst precursor may be activated by any of the conventional activation processes. For instance, the catalyst precursor may be activated using a reducing gas, such as hydrogen, a gaseous hydrocarbon, a mixture of hydrogen and a gaseous hydrocarbon (e.g. methane), a mixture of gaseous hydrocarbons, a mixture of hydrogen and gaseous hydrocarbons, a mixture of hydrogen and nitrogen, syngas, or a mixture of syngas and hydrogen.

The gas may be at a pressure of from 1 bar (atmospheric pressure) to 100 bar, or at a pressure of less than 30 bar.

The catalyst precursor may be heated to its activation temperature at a rate of from 0.01 to 20° C. per minute. The activation temperature may be no more than 600° C., or no more than 400° C.

The catalyst precursor may be held at the activation temperature for from 2 to 24 hours, or from 8 to 12 hours.

After activation, the catalyst may be cooled to a desired reaction temperature.

The catalyst, after activation, may be used in a Fischer-Tropsch process. This process may be carried out in a fixed bed reactor, a continuous stirred tank reactor, a slurry bubble column reactor or a circulating fluidized bed reactor. This process may be carried out in a microchannel reactor (or "microreactor").

The Fischer-Tropsch process is well known and the reaction conditions can be any of those known to the person skilled in the art, for instance the conditions discussed in WO 2008/104793. For example the Fischer-Tropsch process may be carried out at a temperature of from 150 to 300° C., or from 200 to 260° C., a pressure of from 1 to 100 bar, or from 15 to 25 bar, a $H_2$ to CO molar ratio of from 1.2 to 2.2 or 1.5 to 2.0 or about 1.8, and a gaseous hourly space velocity of from 200 to 5000, or from 1000 to 2000. In a microchannel reactor, the gaseous hourly space velocity may be from 5000 to 30000.

As used herein the term "microchannel reactor" refers to an apparatus comprising one or more process microchannels wherein a reaction process is conducted. The process may comprise any chemical reaction such as a Fischer-Tropsch Synthesis (FTS) process. When two or more process microchannels are used, the process microchannels may be operated in parallel. The microchannel reactor may include a manifold for providing for the flow of reactants into the one or more process microchannels, and a manifold providing for the flow of product out of the one or more process microchannels. The microchannel reactor may further comprise one or more heat exchange channels adjacent to and/or in thermal contact with the one or more process microchannels. The heat exchange channels may provide heating and/or cooling for the fluids in the process microchannels. The heat exchange channels may be microchannels. The microchannel reactor may include a manifold for providing for the flow of heat exchange fluid into the heat exchange channels, and a manifold providing for the flow of heat exchange fluid out of the heat exchange channels. Examples of microchannel reactors are as described in WO 2009/126769, WO 2008/030467, WO 2005/075606 and U.S. Pat. No. 7,084,180 B2.

The depth of each microchannel may be in the range of about 0.05 to about 10 mm, or from about 0.05 to about 5 mm, or from about 0.05 to about 2 mm, or from about 0.1 to about 2 mm, or from about 0.5 to about 2 mm, or from about 0.5 to about 1.5 mm, or from about 0.08 to about 1.2 mm. The width of each microchannel may be up to about 10 cm, or from about 0.1 to about 10 cm, or from about 0.5 to about 10 cm, or from about 0.5 to about 5 cm.

As used herein in relation to microchannel reactors, the term "contact time" refers to the volume of the reaction zone within the microchannel reactor divided by the volumetric feed flow rate of the reactant composition at a temperature of 0° C. and a pressure of one atmosphere.

Preferably, the microchannel reactor used for the FTS process is capable of high heat flux for cooling of the process microchannels during the reaction, which may be achieved by incorporating heat exchange channels as described above. The microchannel reactor for FTS may be designed to achieve a heat flux greater than 1 W/cm$^2$. The heat flux for convective heat exchange in the microchannel reactor may range from about 1 to about 25 watts per square centimeter of surface area of the process microchannels (W/cm$^2$) in the microchannel reactor, suitably from about 1 to about 10 W/cm$^2$. The heat flux for phase change or simultaneous endothermic reaction heat exchange may range from about 1 to about 250 W/cm$^2$, from about 1 to about 100 W/cm$^2$, from about 1 to about 50 W/cm$^2$, from about 1 to about 25 W/cm$^2$, and from about 1 to about 10 W/cm$^2$.

The cooling of the process microchannels during the reaction is advantageous for controlling selectivity towards the main or desired product due to the fact that such added cooling reduces or eliminates the formation of undesired by-products from undesired parallel reactions with higher activation energies. As a result of this cooling, the temperature of the reactant composition at the entrance to the process microchannels may be within about 200° C., within about 150° C., within about 100° C., within about 50° C., within about 25° C., within about 10° C., of the temperature of the product (or mixture of product and unreacted reactants) at the exit of the process microchannels.

It will be recognised that features related to one aspect of the invention are also, where applicable, features of other aspects of the invention. It will further be recognised that features specified herein in one embodiment of the invention may be combined with other features specified herein to provide further embodiments.

DETAILED DESCRIPTION

The present invention is now described, by way of illustration only, with reference to the accompanying drawings, in which.

Figure 1:
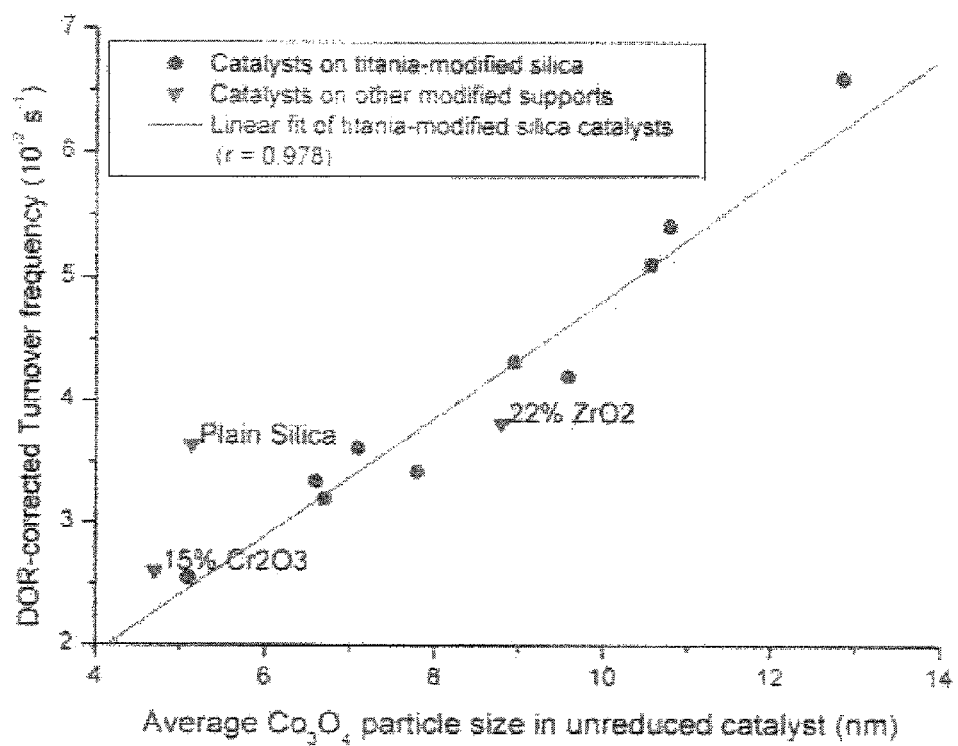
FIG. 1 shows variation in turnover frequency with average $Co_3O_4$ particle size.

The invention is further illustrated by the following examples. It will be appreciated that the examples are for illustrative purposes only and are not intended to limit the invention as described above. Modification of detail may be made without departing from the scope of the invention.

EXAMPLES

The precursor materials used in the preparation of the supports and catalysts of the following Examples are listed in Table 1.

TABLE 1

| Raw Material | Supplier | Other details |
| --- | --- | --- |
| Citric acid monohydrate | Fischer | Purity 99.5% |
| Zirconium dinitrate oxide hydrate | Alfa Aesar | Purity 99.90% |

TABLE 1-continued

| Raw Material | Supplier | Other details |
| --- | --- | --- |
| Silica, SG432 (LC150) | Grace Davison | Particle size 180-300 μm |
| Manganese (II) nitrate tetrahydrate | Alfa Aesar | Purity 98% |
| Chromium (III) nitrate nonahydrate | Sigma Aldrich | Purity 99% |
| Cobalt nitrate hexahydrate | Sigma Aldrich | Purity 98% |
| Tetraammine platinum hydroxide | Alfa Aesar | 9.3% Pt w/w |
| Perrhenic acid | Sigma Aldrich | 70 wt % in water |
| TALH (Titanium(IV) bis(ammonium lactato) dihydroxide) | Sigma Aldrich | 50% solution in water |

Preparation of Modified Catalyst Supports

Examples 1 to 8, relate to the preparation of silica catalyst supports modified with one of zirconium oxide, chromium oxide, and manganese oxide and to catalysts prepared from the catalyst supports. The amounts of the metal precursor used were chosen to give 4 metal atoms per nm$^2$ over the resulting support, except in the case of the 17% $ZrO_2$ support where there are 3 metal atoms per nm$^2$. For each metal, two modified supports were prepared, one using Method A (the "aqueous method") and the other using Method B (the "standard incipient wetness impregnation method"). In Method A, catalyst supports were prepared in which the metal precursor was mixed with an aqueous solution of citric acid (molar ratio of metal atoms to citric acid 1:0.6) and then used to impregnate the support. In Method B, catalyst supports were prepared in which an aqueous solution of only the metal precursor was used to impregnate the support.

Example 1

Synthesis of $ZrO_2$-Modified Silica Catalyst Support (22% $ZrO_2/SiO_2$) Using Method A (Supports A1 to A3)

Silica bare catalyst support material was dried at 100° C. for 2 hours. 31.4 g of silica was weighed and allowed to cool to room temperature. 8.82 g citric acid was mixed with 12 ml $H_2O$ and heated to about 50° C. with stirring until fully dissolved. The solution was then allowed to cool to room temperature. 16.22 g zirconium dinitrate oxide hydrate (also known as "zirconyl nitrate") was mixed with 15 ml $H_2O$ and stirred using a magnetic stirbar, without heat, for 20 minutes to obtain a translucent solution. The zirconyl nitrate solution and citric acid solution were mixed together to form the impregnation solution. The impregnation solution was used immediately after preparation to impregnate the silica support. The support was impregnated by mixing the impregnation solution and the silica in order to reach the point of incipient wetness.

Following impregnation, a portion of the modified catalyst support was dried in a muffle furnace at a temperature that increased at a ramp rate of 2° C./min up to 100° C. The temperature was held at 100° C. for 10 hours (support A1, code 1112-13-005-3).

Further portions of the impregnated support were calcined to different temperatures in order to examine the effect of calcination temperature.

One portion of the impregnated support was calcined at a temperature that increased at a ramp rate of 2° C./min up to 100° C. The temperature was held at 100° C. for 5 hours. The temperature was then increased at a ramp rate of 2° C./min up to 250° C. The temperature was held at 250° C. for 5 hours (support A2, code 1203-21-005-2).

Another portion of the impregnated support was calcined at a temperature that increased at a ramp rate of 2° C./min up to 100° C. The temperature was held at 100° C. for 5 hours. The temperature was then increased at a ramp rate of 2° C./min up to 350° C. The temperature was held at 350° C. for 8 hours (support A3, code 1112-13-005-1).

The resulting catalyst supports A1 to A3 had $ZrO_2$ bound to the silica surface at an amount equivalent to 22% $ZrO_2$ on silica support.

Example 2 (Reference)

Synthesis of $ZrO_2$-Modified Silica Catalyst Support (22% $ZrO_2/SiO_2$) Using Method B (Support B)

Silica bare catalyst support material was dried at 100° C. for 2 hours. 31.4 g of silica was weighed and allowed to cool to room temperature. The impregnation solution was prepared by mixing 16.22 g zirconyl nitrate with 30 ml $H_2O$ and stirring using a magnetic stirbar, without heat, for 20 minutes to obtain a translucent solution with a total volume of 33 ml. The impregnation solution was used immediately after preparation to impregnate the silica support. The support was impregnated by mixing the impregnation solution and the silica in order to reach the point of incipient wetness.

Following impregnation, the modified catalyst support was dried in a muffle furnace at a temperature that increased at a ramp rate of 2° C./min up to 100° C. The temperature was held at 100° C. for 10 hours (support B, code 1112-13-005-4).

The resulting catalyst support B had $ZrO_2$ bound to the silica surface at an amount equivalent to 22% $ZrO_2$ on the silica support.

Example 3

Synthesis of $Mn_2O_3$-Modified Silica Catalyst Support (15% $Mn_2O_3/SiO_2$) Using Method A (Support C)

Silica bare catalyst support material was dried at 100° C. for 2 hours. 16.8 g of silica was weighed and allowed to cool to room temperature. 4.71 g citric acid was mixed with 8 ml $H_2O$ and heated to about 50° C. with stirring until fully dissolved. The solution was cooled to about 35° C., then 9.57 g of manganese nitrate was added and the solution was stirred until fully dissolved. The volume of the solution was adjusted to 19 ml with $H_2O$ to form the impregnation solution and then allowed to cool to room temperature. The impregnation solution was used to impregnate the silica support by mixing the impregnation solution and the silica in order to reach the point of incipient wetness.

Following impregnation, the modified catalyst support was dried in a muffle furnace at a temperature that increased at a ramp rate of 2° C./min up to 100° C. The temperature was held at 100° C. for 10 hours (support C, code 1112-14-005-3).

The resulting modified catalyst support C had $Mn_2O_3$ bound to the silica surface at an amount equivalent to 15% $Mn_2O_3$ on silica support.

Example 4 (Reference)

Synthesis of $Mn_2O_3$-Modified Silica Catalyst Support (15% $Mn_2O_3/SiO_2$) Using Method B (Support D)

Silica bare catalyst support material was dried at 100° C. for 2 hours. 16.8 g of silica was weighed and allowed to cool to room temperature. 9.57 g of manganese nitrate was added to 8 ml $H_2O$ and heated to about 35° C. with stirring until fully dissolved. The volume of the solution was adjusted to 19 ml with $H_2O$ to form the impregnation solution and then allowed to cool to room temperature. The impregnation solution was used to impregnate the silica support by mixing the impregnation solution and the silica in order to reach the point of incipient wetness.

Following impregnation, the modified catalyst support was dried in a muffle furnace at a temperature that increased at a ramp rate of 2° C./min up to 100° C. The temperature was held at 100° C. for 10 hours (support D, code 1112-14-005-4).

The resulting modified catalyst support C had $Mn_2O_3$ bound to the silica surface at an amount equivalent to 15% $Mn_2O_3$ on silica support.

Example 5

Synthesis of $Cr_2O_3$-Modified Silica Catalyst Support (15% $Cr_2O_3/SiO_2$) Using Method A (Support E)

Silica bare catalyst support material was dried at 100° C. for 2 hours. 17.1 g of silica was weighed and allowed to cool to room temperature. 4.81 g citric acid was mixed with 5 ml $H_2O$ and heated to about 50° C. with stirring until fully dissolved. The citric acid solution was cooled to room temperature and then 15.42 g of chromium nitrate was added and the solution heated gently until fully dissolved. The solution was cooled, thereby forming the impregnation solution. The impregnation solution was used to impregnate the silica support by mixing the impregnation solution and the silica in order to reach the point of incipient wetness.

Following impregnation, the modified catalyst support was dried in a muffle furnace at a temperature that increased at a ramp rate of 2° C./min up to 100° C. The temperature was held at 100° C. for 10 hours (support E, code 1203-09-005-3).

The resulting modified catalyst support E had $Cr_2O_3$ bound to the silica surface at an amount equivalent to 15% $Cr_2O_3$ on silica support.

Example 6 (Reference)

Synthesis of $Cr_2O_3$-Modified Silica Catalyst Support (15% $Cr_2O_3/SiO_2$) Using Method B (Support F)

Silica bare catalyst support material was dried at 100° C. for 2 hours. 17.1 g of silica was weighed and allowed to cool to room temperature. 15.42 g of chromium nitrate was added to 5 ml $H_2O$ and the solution heated gently until fully dissolved. The solution was cooled. The volume of the solution was adjusted with $H_2O$ to 19 ml to form the impregnation solution. The impregnation solution was used to impregnate the silica support by mixing the impregnation solution and the silica in order to reach the point of incipient wetness.

Following impregnation, the modified catalyst support was dried in a muffle furnace at a temperature that increased at a ramp rate of 2° C./min up to 100° C. The temperature was held at 100° C. for 10 hours (support H, code 1203-09-005-4).

The resulting modified catalyst support F had $Cr_2O_3$ bound to the silica surface at an amount equivalent to 15% $Cr_2O_3$ on silica support.

Example 7

Synthesis of $ZrO_2$-Modified Silica Catalyst Support (17% $ZrO_2/SiO_2$) Using Method A (Support G)

Silica bare catalyst support material was dried at 100° C. for 2 hours. 16.6 g of silica was weighed and allowed to cool to room temperature. 3.5 g citric acid was mixed with 5 ml $H_2O$ and heated to about 50° C. with stirring until fully dissolved. The solution was then allowed to cool to room temperature. 6.42 g zirconium dinitrate oxide hydrate (also known as "zirconyl nitrate") was mixed with 9 ml $H_2O$ and stirred using a magnetic stirbar, without heat, for 20 minutes to obtain a translucent solution. The zirconyl nitrate solution and citric acid solution were mixed together to form the impregnation solution of total volume about 19 ml. The impregnation solution was used immediately after preparation to impregnate the silica support. The support was impregnated by mixing the impregnation solution and the silica in order to reach the point of incipient wetness.

Following impregnation, the modified catalyst support was dried in a muffle furnace at a temperature that increased at a ramp rate of 2° C./min up to 100° C. The temperature was held at 100° C. for 10 hours (support G, code 1203-06-005-7).

The resulting catalyst support G had $ZrO_2$ bound to the silica surface at an amount equivalent to 17% $ZrO_2$ on silica support.

Example 8 (Reference)

Synthesis of $ZrO_2$-Modified Silica Catalyst Support (17% $ZrO_2/SiO_2$) Using Method B (Support B)

Silica bare catalyst support material was dried at 100° C. for 2 hours. 16.6 g of silica was weighed and allowed to cool to room temperature. The impregnation solution was prepared by mixing 6.42 g zirconyl nitrate with 16 ml $H_2O$ and stirring using a magnetic stirbar, without heat, for 20 minutes to obtain a translucent solution with a total volume of 19 ml. The impregnation solution was used immediately after preparation to impregnate the silica support. The support was impregnated by mixing the impregnation solution and the silica in order to reach the point of incipient wetness.

Following impregnation, the modified catalyst support was dried in a muffle furnace at a temperature that increased at a ramp rate of 2° C./min up to 100° C. The temperature was held at 100° C. for 10 hours (support H, code 1203-06-005-8).

The resulting catalyst support H had $ZrO_2$ bound to the silica surface at an amount equivalent to 17% $ZrO_2$ on the silica support.

Synthesis of Catalysts from Modified Supports

Example 9

A catalyst was prepared from each of the modified catalyst supports made using Method A (Examples 1, 3, 5 and 7, except for support A3).

For each modified support, an impregnation solution was prepared by dissolving 12.75 g cobalt nitrate hexahydrate in 3 ml $H_2O$ and heating to about 50° C. with stirring until fully dissolved. The solution was cooled to room temperature and 0.024 g perrhenic acid was added. $H_2O$ was added to make the volume of the solution 11 ml.

A first impregnation of each support was carried out by using the 11 ml of impregnation solution to impregnate about 11.7 g of the support (support purity estimated at 85% to give a final support weight of 10 g). The impregnated modified catalyst support was then dried at a temperature that increased at a ramp rate of 2° C./min up to 100° C. The temperature was held at 100° C. for 5 hours. The modified catalyst support was subsequently calcined by increasing the temperature to 250° C. using a ramp rate of 2° C./min and holding the temperature at 250° C. for 3 hours.

Second, third and fourth impregnation steps of each modified catalyst support were carried out by preparing, for each modified catalyst support, a stock impregnation solution of 5.78 g citric acid mixed with 4 ml $H_2O$ and heating to about 50° C. with stirring until fully dissolved. This solution was added to 40.71 g cobalt nitrate hexahydrate and heated to about 50° C. with stirring until fully dissolved. To this was added 0.077 g perrhenic acid and the solution was cooled to room temperature. The resulting stock impregnation solution was divided over impregnation steps 2 to 4, as shown in Table 2, which summarises the four impregnation steps. After each impregnation step, the modified catalyst support was calcined at a temperature that increased at a ramp rate of 2° C./min up to 100° C. The temperature was held at 100° C. for 5 hours. The modified support catalyst was subsequently calcined by increasing the temperature to 250° C. using a ramp rate of 2° C./min and holding the temperature at 250° C. for 3 hours.

TABLE 2

| Step | Support wt (g) | $Co(NO_3)_2$ $6H_2O$ (g) Purity 98% | $Co(NO_3)_2$ $6H_2O$ (g) *Purity 100% | $Co_3O_4$ (g) | Co (g) | Citric acid (g) | Perrhenic acid (g) | Re (g) | $H_2O$ (ml) | Solution volume (ml) | Calc. Wt (g) | % Co |
|---|---|---|---|---|---|---|---|---|---|---|---|---|
| 1 | 10 | 12.75 | 12.49 | 3.44 | 2.53 | 0.00 | 0.0242 | 0.0117 | min. | 11.0 | 13.5 | 18.8 |
| 2 | — | 13.57 | 13.3 | 3.67 | 2.69 | 1.93 | 0.0258 | 0.0124 | min. | 10.0 | 17.1 | 30.5 |
| 3 | — | 13.57 | 13.3 | 3.67 | 2.69 | 1.93 | 0.0258 | 0.0124 | min. | 9.5 | 20.8 | 38.0 |
| 4 | — | 13.57 | 13.3 | 3.67 | 2.69 | 1.93 | 0.0258 | 0.0124 | min. | 8.0 | 24.5 | 43.3 |

*This is a calculated value to show how much $Co(NO_3)_2 \cdot 6H_2O$ is actually added.

After the impregnation step 4 and the last calcination, each resulting catalyst precursor was subjected to a promoter addition step. 0.048 g of tetraammine platinum hydroxide (9.3% Pt w/w) was diluted to 3.4 ml with water to make a dilute solution and this solution was used to further impregnate 15 g of the catalyst precursor. After impregnation, the catalyst was then dried at a temperature that increased at a ramp rate of 2° C./min up to 100° C. The temperature was held at 100° C. for 5 hours. The catalyst was subsequently calcined by increasing the temperature to 250° C. using a ramp rate of 2° C./min and holding the temperature at 250° C. for 3 hours.

Each of the resulting catalysts made from a Method A support had 0.03% Pt and is suitable for use as, for example, a Fischer-Tropsch catalyst.

Example 10

A catalyst was prepared from each of the modified catalyst supports made using Method B (Examples 2, 4, 6 and 8) and the modified catalyst support made from Method A but calcined to 350° C. (Support A3).

For each modified support, a stock impregnation solution was prepared by mixing 7.24 g citric acid with 6 ml $H_2O$ and heating to about 50° C. with stirring until fully dissolved. This solution was added to 50.98 g cobalt nitrate hexahydrate and heated to about 50° C. with stirring until fully dissolved. 0.099 g perrhenic acid was added and the solution was cooled to room temperature For each modified catalyst support, the stock impregnation solution was dived over each of four impregnation steps, as summarised in Table 3. For the first impregnation step 11.7 g of the support (support purity estimated at 85% to give a final support weight of 10 g) was used. After each of impregnation steps 1 to 4, the impregnated modified catalyst support was dried at a temperature that increased at a ramp rate of 2° C./min up to 100° C. The temperature was held at 100° C. for 5 hours. The modified catalyst support was subsequently calcined by increasing the temperature to 250° C. using a ramp rate of 2° C./min and holding the temperature at 250° C. for 3 hours.

TABLE 3

| Step | Support wt (g) | Co(NO$_3$)$_2$ 6H$_2$O (g) Purity 98% | Co(NO$_3$)$_2$ 6H$_2$O (g) Purity 100% | Co$_3$O$_4$ (g) | Co (g) | Citric acid (g) | Perrhenic acid (g) | Re (g) | H$_2$O (ml) | Solution volume (ml) | Calc. Wt (g) | % Co |
|---|---|---|---|---|---|---|---|---|---|---|---|---|
| 1 | 10 | 12.75 | 12.49 | 3.44 | 2.53 | 1.81 | 0.0247 | 0.0119 | min. | 10.0 | 13.5 | 18.8 |
| 2 | — | 12.75 | 12.49 | 3.44 | 2.53 | 1.81 | 0.0247 | 0.0119 | min. | 10.0 | 16.9 | 39.9 |
| 3 | — | 12.75 | 12.49 | 3.44 | 2.53 | 1.81 | 0.0247 | 0.0119 | min. | 9.0 | 20.4 | 37.2 |
| 4 | — | 12.75 | 12.49 | 3.44 | 2.53 | 1.81 | 0.0247 | 0.0119 | min. | 9.0 | 23.8 | 42.4 |

After the impregnation step 4 and the last calcination, each resulting catalyst precursor was subjected to a promoter addition step. 0.048 g of tetraammine platinum hydroxide (9.3% Pt w/w) was diluted to 3.4 ml with water to make a dilute solution and this solution was used to further impregnate 15 g of the catalyst precursor. After impregnation, the catalyst was then dried at a temperature that increased at a ramp rate of 2° C./min up to 100° C. The temperature was held at 100° C. for 5 hours. The catalyst was subsequently calcined by increasing the temperature to 250° C. using a ramp rate of 2° C./min and holding the temperature at 250° C. for 3 hours.

Each of the resulting catalysts made from a Method B support had 0.03% Pt and is suitable for use as, for example, a Fischer-Tropsch catalyst.

Comparison of Catalysts Made from a Method A Support and a Method B Support

Example 11

Fischer-Tropsch Reaction Tests

Catalysts obtained in Examples 9 and 10 were tested for Fischer Tropsch synthesis (FTS) performance. The catalysts were diluted with SiC at a 1:18 ratio and then loaded in a fixed-bed combinatorial reactor (L/D 31 cm) and reduced using pure hydrogen at 400° C. for 120 minutes at Gas Hourly Space Velocity (GHSV)=15 000 per hour. The temperature was increased from room temperature to 400° C. at 1° C./min. After the reduction, the reactor was cooled to 165° C. and the gas was switched from hydrogen to synthesis gas. The operating conditions were kept constant for 1 hour. The pressure was then increased to 20 bar at the flow rate of the reaction and held for 1 hour. The temperature was then increased from 165° C. to 190° C. at a ramp rate of 4° C./hour, from 190 to 210° C. (GHSV=12 400 per hour) at 2° C./hour and then kept at 210° C. (GHSV=12 400 per hour) for about 120 hours. The Fischer Tropsch reaction was carried out for a total of 160 hours.

The deactivation rate of the catalyst was calculated via a linear regression analysis of the percent of CO converted during the reaction between a time on stream of 24 hours until the end of the run (160 hours). The activity of the catalyst, in mol CO hr$^{-1}$ g$_{Co}$$^{-1}$, at 24 hours time on stream was calculated via $$\text{activity} = \frac{\text{CO \% conversion}}{100\%} \cdot \frac{\text{CO flow rate in } \frac{mL}{min} \cdot 60 \frac{min}{hr}}{22400 \frac{mL}{mol\ CO}} \cdot \frac{1}{\text{catalyst weight in g} \cdot 0.42}$$

The temperature at which the FT reaction test was carried out varied depending on the activity of the catalyst. Catalysts were tested initially at 210° C. Catalysts displaying high activity were also tested at 203° C. in order to compare FTS performance of catalysts with differing activities at similar conversion levels.

A summary of the FTS performance of the catalysts is shown in Table 4 and compared to a reference titania-modified silica made using the aqueous method.

TABLE 4

| Support used | % CO conversion | Δ % CO conversion (%/day) | Selectivity (%) C$_{5+}$ | Selectivity (%) CH$_4$ | Activity mol CO/hr/g Co | Run # | ρ (g/ml) | T (° C.) |
|---|---|---|---|---|---|---|---|---|
| Titania-modified silica (reference) | 73.6 | −1.12 | 86.4 | 9.3 | 0.273 | 69 | 1.12 | 210 |
| Support A1 (22% ZrO$_2$, method A, dried 100° C.) | 80.7 | −1.41 | 86.2 | 9.2 | 0.266 | 69 | 1.26 | 210 |
| Support A1 (22% ZrO$_2$, method A, dried 100° C., repeat preparation) | 74.6 | −0.83 | 86.1 | 9.2 | 0.222 | 76 | 1.39 | 203 |
| Support A1 (22% ZrO$_2$, method A, dried 100° C.) | 65.8 | −1.08 | 87.5 | 7.7 | 0.216 | 76 | 1.26 | 203 |
| Support A2 (22% ZrO$_2$, method A, calcined 250° C.) | 83.2 | −1.43 | 87.3 | 8.8 | 0.278 | 69 | 1.24 | 210 |
| Support A2 (22% ZrO$_2$, method A, calcined 250° C.) | 69.1 | −1.01 | 87.4 | 8.3 | 0.231 | 76 | 1.24 | 203 |

TABLE 4-continued

| Support used | % CO conversion | Δ % CO conversion (%/day) | Selectivity (%) $C_{5+}$ | $CH_4$ | Activity mol CO/hr/g Co | Run # | ρ (g/ml) | T (° C.) |
|---|---|---|---|---|---|---|---|---|
| Support A3 (22% $ZrO_2$, method A, calcined 350° C.) | 77.1 | −1.54 | 87.8 | 8.8 | 0.281 | 69 | 1.14 | 210 |
| Support B (22% $ZrO_2$, method B) | 74.3 | −1.74 | 87.8 | 8.7 | 0.266 | 65 | 1.16 | 210 |
| Support C (15% $Mn_2O_3$, method A, dried 100° C.) | 12.7 | −0.42 | 55.0 | 11.3 | 0.043 | 65 | 1.21 | 210 |
| Support E (15% $Cr_2O_3$, method A, dried 100° C.) | 71.3 | −2.22 | 85.0 | 10.1 | 0.238 | 69 | 1.24 | 210 |
| Support F (15% $Cr_2O_3$, method B) | 76.9 | −2.10 | 85.6 | 10.3 | 0.242 | 72 | 1.32 | 210 |
| Support G (17% $ZrO_2$, method A, dried 100° C.) | 66.7 | −0.94 | 85.2 | 7.9 | 0.208 | 76 | 1.33 | 203 |
| Support H (17% $ZrO_2$, method B) | 63.5 | −0.99 | 86.5 | 7.9 | 0.221 | 76 | 1.19 | 203 |

The results show that catalysts made using the zirconia-modified supports display particularly good FTS performance, comparable to a reference catalyst made using a titania-modified silica catalyst support.

The catalyst made on a support modified with 22% $ZrO_2$ via Method A shows an improvement in stability over the reference catalyst made using a titania-modified silica support. The stability of the catalyst on zirconium oxide-modified silica is shown to vary depending on the temperature at which the support was pretreated. The stability of the catalyst is highest when the support is either dried only or treated to 250° C.; a significant decrease in stability is observed when the support is calcined to 350° C. However, even the support treated to 350° C. is more stable than the catalyst made on silica modified with 22% $ZrO_2$ via Method B. The catalyst made on the Method B 22% $ZrO_2/SiO_2$ support has a deactivation rate that is approximately twice as fast as the catalyst on the Method A support. Additionally, the catalysts on the Method A supports which were either dried or calcined to just 250° C. are more active than either the reference catalyst on titania-modified silica or the Method B 22% $ZrO_2/SiO_2$ supports. The increased activity of the catalysts on the supports modified using Method A is shown by the lower temperature used during FTS to reach similar conversion levels. Without being bound by theory, the inventors believe that the residual organic species on the modified support are a factor in making the catalysts derived from Method A supports more stable. The higher the pretreatment temperature, the fewer organic species remain on the surface of the support, which results in a decrease in stability.

In addition to the increase in stability and activity of the catalysts on 22% $ZrO_2/SiO_2$, there is an unexpected decrease in the methane selectivity of these catalysts as compared to the reference catalyst made using a titania-modified silica support. All the catalysts on a 22% $ZrO_2/SiO_2$ support have a methane selectivity that is lower than the reference catalyst on titania-modified silica.

The catalysts on 17% $ZrO_2$ modified silica made by Method A is more stable than the catalyst on the Method B support but the magnitude of the difference is much less than was observed for 22% $ZrO_2$. This indicates that a minimum level of metal oxide modifier may be required to observe a substantial increase in stability. However, the 17% $ZrO_2$ catalyst is more active than the reference titania-modified silica catalyst, as shown by the decreased temperature used during FTS testing.

The catalysts on supports modified with 15% $Cr_2O_3$ made using Method A and Method B are both more unstable during FTS than the zirconium oxide-modified support.

In summary, catalysts made using $ZrO_2$-modified silica supports prepared using Method A are more stable than those prepared using Method B. Furthermore, comparison of the catalysts made using $ZrO_2$-modified silica supports shows that calcining at 250° C. is advantageous compared to calcining at 350° C. or to simply drying at 100° C. and leads to more stable catalysts.

Example 12

Comparison of Porosity and Acidity of Modified Supports Prepared in Examples 1 to 6

The BET surface areas of the modified supports prepared in Examples 1 to 6 were determined using nitrogen physisorption at 77K in a Micromeritics Tristar II instrument. All supports were calcined to 400° C. before measurement. Prior to measurement, all samples were degassed in nitrogen at 100 C for 3 hours. The pore size distribution, average pore size and total pore volume were determined using a density functional theory (DFT) calculation method, with adsorption isotherm pressure points over the range 0.25 to 0.99 p/po. A Micromeritics built-in cylindrical model based on oxide surfaces was chosen, and a high degree of regularisation applied. The results of this analysis are shown in Table 5.

To determine the acidity of the modified support surface of the modified supports prepared in Examples 1 to 6, temperature programmed desorption (TPD) experiments were carried out using an Altamira AMI200 instrument. All modified supports were calcined to 400° C. before measurement. About 50 mg of the modified support sample was loaded into a U-shaped quartz tube, with a small wad of quartz wool above and below the sample. The samples were first degassed in argon at 150° C. for 30 minutes, before decreasing the temperature to 100° C. and changing the flow to 10% $NH_3$ in helium. This gas mixture was passed over the sample of modified catalyst support at 100° C. for 30 minutes (analysis of the TCD signal indicated gas absorption was complete within a few minutes), before switching back to argon. Inert gas flow was maintained for 1 hour to remove physisorbed species after which the temperature was then reduced to 70° C. The desorption was carried out under flowing argon from 70 to 400° C. at 5° C./min, followed by a hold at 400° C. for 30 minutes. A moisture trap was not used. Quantification of the amount of gas released was carried out by calibration of a 10% $NH_3$ in a stream of helium. The results of this analysis are shown in Table 5.

The results show that the method of modifying the support has a significant effect on the porosity of the resulting catalysts. The catalyst supported on 22% $ZrO_2/SiO_2$, Method A, has a lower pore volume and a smaller average pore diameter than the catalyst supported on the 22% $ZrO_2/SiO_2$ support made via Method B. The same trend is observed for the catalysts supported on 17% $ZrO_2/SiO_2$. Although the catalysts on 15% $Cr_2O_3/SiO_2$ supports have very similar pore

TABLE 5

| | Method A supports | | | Method B supports (reference) | | |
|---|---|---|---|---|---|---|
| | 22% $ZrO_2$ | 15% $Mn_2O_3$ | 15% $Cr_2O_3$ | 22% $ZrO_2$ | 15% $Mn_2O_3$ | 15% $Cr_2O_3$ |
| BET As ($m^2/g$) | 299.65 | 291.18 | 274.74 | 292.58 | 278.51 | 273.70 |
| DFT pore volume ($cm^3/g$) | 0.9183 | 0.9444 | 0.9748 | 0.9316 | 0.9802 | 1.018 |
| DFT Av pore diameter (Å) | 171.1 | 183.73 | 174.78 | 193.2 | 189.85 | 183.82 |
| Surface acidity (µmol $NH_3/m^2$) | 0.120 | 0.251 | 0.282 | — | — | — |

The results summarised in Table 5 show that when Method A is used to modify silica, the resulting catalyst supports have higher surface areas and smaller average pore diameters than supports modified using Method B. It is believed that the use of an aqueous metal precursor and citric acid is more effective at dispersing the metal oxides over the support than the use of the standard incipient wetness impregnation method (Method B).

The results also show that the porosity and the surface acidity of the supports varies significantly as the metal used to modify the support is varied. This shows that modifying silica with a metal oxide offers a way to alter the porosity and acidity of the support and, as such, specific surface acidity and/or porosity properties of silica can be obtained by selecting the metal species used to modify the catalyst support.

Example 13

Comparison of Porosity of Catalysts Made from the Modified Supports

The BET surface area of catalysts obtained in Examples 9 and 10 was determined using nitrogen physisorption at 77 K in a Micromeritics Tristar II instrument. Prior to measurement, all samples were degassed in nitrogen at 100° C. for 3 hours. The pore size distribution, average pore size and total pore volume were determined using a DFT calculation method, with adsorption isotherm pressure points over the range 0.25-0.99 p/po. A Micromeritics built-in cylindrical model based on oxide surfaces was chosen, and a high degree of regularisation applied. The porosities of catalysts made from the modified silica supports are shown in Table 6.

volumes, the catalyst on the Method B support has a larger average pore diameter than the catalyst on the Method A support.

For all three comparisons, the catalyst on the Method B support has a larger pore diameter than the catalyst on the Method A support. This indicates that the dispersion through the Method A supported catalysts differs from the Method B supported catalysts.

When Method B is used to prepare the modified catalyst support, the resulting catalysts have larger pore diameters and the catalyst components are less well dispersed through the particle pores than when Method A is used. Without being bound by theory, the inventors believe that a better dispersion of the metal oxide through the catalyst support material results in a more effective coverage of hydroxyl groups on the silica surface, thus resulting in a more stable catalyst.

Example 14

Comparison of $Co_3O_4$ Particle Size of Catalysts Made from the Modified Supports X-ray diffraction patterns of fresh catalysts obtained in Examples 9 and 10 were collected on a fully automated Siemens D5000 theta/theta powder diffractometer using Cu $K_\alpha$ radiation. Each sample was ground thoroughly before loading into a spinner carousel in air. Data were collected over the range 10-80° 2θ, with a step size of 0.05° and a step length of 12 s, and were analysed using the Rietveld method via the program GSAS. Likely crystalline phases were included until all peaks were indexed. The average $Co_3O_4$ crystallite size

TABLE 6

| | Method A supports | | | | Method B supports (reference) | | |
|---|---|---|---|---|---|---|---|
| | 22% $ZrO_2$ | 22% $ZrO_2$, calc 250° C. (Support A2) | 17% $ZrO_2$ (Support G) | 15% $Cr_2O_3$ (Support E) | 22% $ZrO_2$ (Support B) | 17% $ZrO_2$ (Support H) | 15% $Cr_2O_3$ (Support F) |
| | (support A1) | | | | | | |
| BET As ($m^2/g$) | 104 | 111 | 95.7 | 114 | 111 | 116 | 107 |
| DFT pore volume ($cm^3/g$) | 0.219 | 0.233 | 0.226 | 0.223 | 0.251 | 0.286 | 0.214 |
| DFT Av pore diameter (Å) | 136 | 144 | 149 | 127 | 158 | 157 | 140 |

($D_O$), the c value and the D value of the $Co_3O_4$ crystallites were determined as described below.

The lattice parameters and phase fractions of all phases were refined first along with the background, which was fitted with a 16 term shifted Chebyshev polynomial. The sample shift and transparency were freely refined. As $Co_3O_4$ was the major phase in all calcined catalysts studied, this phase was analysed in detail. The oxygen atom position of the $Co_3O_4$ phase was first refined, along with the thermal parameters of all positions in this phase. The profile shape of the $Co_3O_4$ phase was then fitted with a Caglioti instrumental function (previously determined using a corundum standard) and a Lorentzian X and Y term were refined along with a Gaussian U and P contribution. The X, Y, U and P profile parameters of the $Co_3O_4$ phase were deconvoluted into their size and strain components using the methods described in Balzar et al. Journal of Applied Crystallography (2004), 37, 911-924 and Krill et al, Philosophical Magazine A (1998) 77, 620-640.

Explicitly, the X and P profile shape terms were used to determine the average crystallite size and the width of the distribution (assuming a lognormal, monomodal size distribution of spherical crystallites). First, the profile parameters were converted into integral breadths via $$\beta_{G,S} = \frac{\sqrt{2\pi^3 P}}{18000}$$

$$\beta_{L,S} = \frac{\pi^2 X}{2 \cdot 18000}$$

The Lorentzian and Gaussian integral breadths are then combined for the size (S) part:

$$\beta_S = \frac{\beta_{G,S} e^{-k_s^2}}{1 - \mathrm{erf}(k_s)} \text{ where } k_s = \frac{\beta_{L,S}}{\sqrt{\pi}\beta_{G,S}}$$

Once the separate peak shapes have been deconvoluted into the size component via this method, the volume-weighted ($L_V$, size distribution function weighted by the volume of the domains) and area-weighted ($L_A$, size distribution function weighted by the cross-sectional area of the domains) domain sizes may be determined through $$L_V = \frac{\lambda}{\beta_S} \text{ and } L_A = \frac{\lambda}{2\beta_{L,S}}$$

If the crystallites are assumed to be spheres, the area- and volume-weighted domain sizes can be related to the sphere diameters via $$D_V = 4/3 L_V \text{ and } D_A = 3/2 L_A$$

Finally, the volume and area weighted domain sizes are related to the dimensionless ratio c of the lognormal distribution and the numeric average particle radii $R_O$ by $$c = \frac{8L_V}{9L_A} - 1 \text{ and } R_O = \frac{2L_V}{3(1+c)^3}$$

This explicitly assumes that the real particles are equivalent to the crystallites. The numeric average particle diameter ($D_O = 2R_O$) is thus related to the volume- and area-weighed diameters through $$D_V = D_O(1+c)^3 \text{ and } D_A = D_O(1+c)^2$$

The form of the distribution is:

$$f(R) = \frac{1}{R\sqrt{2\pi \ln(1+c)}} e^{-\frac{[\ln(\frac{R}{R_O}\sqrt{1+c})]^2}{2\ln(1+c)}} \text{ where } c = \frac{\sigma^2}{R_O^2} \quad \text{Equation 1}$$

Where $R_O$ is the numeric average particle radius and c, which is known as the dimensionless ratio, characterises the width of the size distribution.

The frequency at the mode of this lognormal distribution ($f_{mode}$) modelled using Equation 1 was weighted by the size distribution median to create a "size-weighted distributed breadth", or D-value, using the formula:

$$D = f_{mode}{}^y \times R_O \times 2 \quad \text{Equation 2}$$

wherein $f_{mode}$ is the frequency at the mode of the lognormal distribution; y is an exponential factor which is determined experimentally to obtain the best degree of fit with the FTS stability data, as described above, and $R_O$ is the numeric average particle radius.

The D-value provides a characterisation of the width of the size distribution.

TABLE 7

| | Catalysts on Method A supports | | Catalysts on Method B supports (reference) | | Catalyst on |
|---|---|---|---|---|---|
| | 22% | | 22% | 15% | titania |
| | $ZrO_2$, calc 250° C. (Support A2) | 15% $Cr_2O_3$ (Support E) | $ZrO_2$ (Support B) | $Cr_2O_3$ (Support F) | modified silica support (reference) |
| Average particle size (nm) | 8.8(8) | 4.7(9) | 9.3(9) | 5.8(6) | 7.1(4) |
| c value | 0.23(2) | 0.29(3) | 0.23(3) | 0.22(2) | 0.33(2) |
| D value | 21.8 | 21.9 | 21.8 | 23.9 | 19.7 |

It is clear from Table 7 that there is significant scatter in the D-value of the modified silica supports and, in conjunction with Table 4, this value does not appear to correlate readily with deactivation rate. The catalyst on 22% $ZrO_2/SiO_2$ (method A, dried to 100° C.) and the catalyst on 15% $Cr_2O_3/SiO_2$ (method A, dried to 100° C.) have very similar D-values but their deactivation rates, as shown in Table 4, are very different. This may indicate that the correlation developed between D-value and deactivation rate may be sensitive to the nature of the catalyst support.

The results show that the method of modifying the catalyst support has only a small effect on the resulting $Co_3O_4$ particle size of the catalyst. For the catalyst supported on 22% $ZrO_2/SiO_2$, using Method A to deposit zirconia results in a catalyst with slightly smaller $Co_3O_4$ particles than using Method B. The same trend is observed for the catalyst supported on 15% $Cr_2O_3/SiO_2$. However, in both cases, the difference between the $Co_3O_4$ size on the catalysts made with Method A and Method B supports is within the error of the measurement. This suggests that using Method A (aqueous precursor with citric acid) to deposit the support modifier may result in slightly smaller cobalt oxide crystallites in the resulting catalyst as compared to the use of Method B.

Example 15

Co⁰ Dispersion of Catalysts Made from the Modified Supports

The $Co^0$ surface area was determined via $H_2$ chemisorption on the Micromeritics ASAP 2020c instrument. Approximately 300 mg of samples obtained from Examples 9 and 10 were loaded into a U-shaped quartz tube, with a small wad of quartz wool above and below the sample. The samples were first degassed in helium at 70° C. for 10 minutes, and then evacuated for 1.5 hours. The flow was then changed to $H_2$, and the temperature increased to 400° C. at 1° C./min, and held at that temperature for six hours. After this reduction, the sample was flushed with helium for 1 hour, evacuated, and hydrogen chemisorption was performed at 100° C. A repeat analysis was carried out, and the quantity of gas adsorbed was determined from the difference between the two chemisorptions. The percentage dispersion of $Co^0$ and the metal surface area were determined assuming a total cobalt concentration of 42 wt. %

TABLE 8

| | Method A supports | | | Method B supports (reference) | | |
|---|---|---|---|---|---|---|
| | 22% $ZrO_2$ (Support A2) | 17% $ZrO_2$ (Support G) | 15% $Cr_2O_3$ (Support E) | 22% $ZrO_2$ (Support B) | 17% $ZrO_2$ (Support H) | 15% $Cr_2O_3$ (Support F) |
| % $Co^0$ dispersion | 2.93 | 2.91 | 1.26 | 2.27 | 2.27 | 2.14 |
| $Co^0$ surface area ($m^2$/g sample) | 8.33 | 8.26 | 3.58 | 6.45 | 6.46 | 6.08 |

The results show that the dispersion of $Co^0$ on the catalysts is affected by the method used to modify the support. Comparing the catalysts made using a 22% $ZrO_2/SiO_2$ support, the catalyst made on the support modified via Method A has a higher dispersion of cobalt than the catalyst made on the support modified via Method B. At a lower zirconia loading (17%), the same trend is observed. The results suggest that for both support modification Methods A and B, the change in zirconia loading from 22% to 17% does not have a significant impact on $Co^0$ dispersion.

For the catalyst support on 15% $Cr_2O_3/SiO_2$, there is also a difference in the cobalt dispersion between the catalysts on the support modified using Methods A and B. The catalyst on the Method A support has a lower cobalt dispersion than the catalyst on the Method B support.

These results suggest that both the method of support modification (Method A or B) and the nature of the oxide modifier ($ZrO_2$ or $Cr_2O_3$) has an effect on the dispersion of $Co^0$ metal. The catalysts made from zirconia-modified supports have particularly high % $Co^0$ dispersion.

Example 16

Preparation of Catalyst Using Titania-Modified Silica Support (Reference)

Silica bare catalyst support material was dried at 100° C. for 2 hours. 84 g of silica was weighed and allowed to cool to room temperature. The impregnation solution was made by dissolving 25 g of citric acid in minimum water at about 50° C. with stirring until fully dissolved. The solution was cooled down to less than 30° C. and the citric acid solution was then added to 118 g (97 ml) of titanium (IV) bis(ammonium lactate)dihydroxide solution (TALH) and made up to the required volume of impregnation, which was about 130 ml, with water. The impregnation solution was allowed to cool.

84 g of silica (weight determined after drying) was impregnated via incipient wetness impregnation with the impregnation solution. Following impregnation, the modified catalyst support was dried at a temperature that increased at a ramp rate of 2° C./min up to 100° C. The temperature was held at 100° C. for 5 hours. The modified support catalyst was subsequently calcined by increasing the temperature to 250° C. using a ramp rate of 2° C./min and holding the temperature at 250° C. for 5 hours.

To prepare the catalyst, 25 g of cobalt nitrate was dissolved in a minimum amount of water to achieve dissolution over heat at about 50° C. 0.048 g perrhenic acid was added and the solution cooled to room temperature. The volume was adjusted to 19 ml and used to impregnate 23-24 g of titania modified silica. This was calcined in a muffle furnace according to the following program: ramp at 2° C./min to 100° C. and dwell for 5 hours, ramp at 2° C./min to 200° C. and dwell for 3 hours, then ramp at 1° C./min to 250° C. and dwell for 3 hours.

For impregnation steps 2 to 4, a stock solution was prepared. 12 g citric acid was mixed with $H_2O$ (minimum amount to obtain a clear solution) and heated to about 50° C. with stirring until fully dissolved. This was added to 8.14 g cobalt nitrate and heated to about 50° C. with stirring until fully dissolved. 0.14 g of perrhenic acid was added and the solution cooled to room temperature. The stock impregnation solution was made up to 67 ml and divided over the impregnation steps as shown in Table 9, and calcined after each step using the following program: ramp at 2° C./min to 100° C. and dwell for 5 hours, then ramp at 2° C./min to 250° C. and dwell for 3 hours. After the last impregnation and calcination, the catalyst was promoted with 0.03% Pt. 0.06 g of the tetraamine platinum hydroxide solution was diluted to 9 ml with water and used to impregnate 20 g of catalyst then calcined using the same program as above.

TABLE 9

| Step | Base (g) | $Co(NO_3)_2$ $6H_2O$ (g) Purity 98% | $Co(NO_3)_2$ $6H_2O$ (g) Purity 100% | $Co_3O_4$ (g) | Co (g) | Citic acid (g) | Perrhenic acid (g) | Re (g) | Solution volume (ml) | Calc wt (g) | % Co (approx.) |
|---|---|---|---|---|---|---|---|---|---|---|---|
| 1 | 20 | 24.49 | 24 | 6.62 | 4.86 | 0.00 | 0.0480 | 0.05 | 19 | 26.6 | 18.2 |
| 2 | 27.2 | 27.14 | 26.6 | 7.33 | 5.38 | 3.84 | 0.0480 | 0.05 | 22 | 34.5 | 29.7 |

TABLE 9-continued

| Step | Base (g) | Co(NO$_3$)$_2$ 6H$_2$O (g) Purity 98% | Co(NO$_3$)$_2$ 6H$_2$O (g) Purity 100% | Co$_3$O$_4$ (g) | Co (g) | Citic acid (g) | Perrhenic acid (g) | Re (g) | Solution volume (ml) | Calc wt (g) | % Co (approx.) |
|---|---|---|---|---|---|---|---|---|---|---|---|
| 3 | 34.4 | 27.14 | 26.6 | 7.33 | 5.38 | 3.84 | 0.0480 | 0.05 | 22 | 41.7 | 37.4 |
| 4 | 41.6 | 27.14 | 26.6 | 7.33 | 5.38 | 3.84 | 0.0480 | 0.05 | 22 | 48.9 | 42.9 |

Example 17

Preparation of Catalyst Using Unmodified Silica Support (Reference)

A catalyst was made on a support that was not modified with a metal oxide (eg. bare silica), labelled 1101-06-016-4. The catalyst was prepared by dissolving 15.01 g of citric acid in H$_2$O (minimum amount to achieve clear solution) and heating to about 50° C. with stirring until fully dissolved. The resulting solution was added to 106.12 g cobalt nitrate hexahydrate and heated to about 50° C. with stirring until fully dissolved. 0.19 g of perrhenic acid was added and the solution cooled to room temperature. This stock solution was divided over 4 impregnation steps as shown in Table 10, and calcined after each step: ramp at 2° C./min to 100° C. and dwell for 5 hours, then ramp at 2° C./min to 250° C. and dwell for 3 hours. After the last impregnation and calcination, the catalyst was promoted with 0.03% Pt using tetraamine platinum hydroxide solution diluted with H$_2$O, then calcined using the same program.

Sieved silica, of size 180 to 300 μm, was dried in an oven at 100° C. for 1 hour. Once cool, 21.0 g of the support was impregnated with a titanium isopropoxide solution: 15.5 ml of titanium isopropoxide was diluted to a volume of 29 ml with isopropanol. This solution was added gradually to the support, with stirring. The impregnated yet still free-flowing support was calcined in a muffle furnace at 100° C. for 10 hours via a ramp of 2° C. per minute. The resulting catalyst support was 16% TiO$_2$-modified silica (expressed as a weight percentage of the catalyst support).

Portions of the titania-modified catalyst support (of a variety of scales of batch size) were impregnated via 4 to 8 impregnation steps with a solution of cobalt nitrate hexahydrate and perrhenic acid and a variety of polar organic compounds as the combustion fuel (either citric acid (citric acid:Co ratio of 0.2), acetic acid (acetic acid:Co ratio of 0.45), malic acid (malic acid:Co ratio of 0.26), glutaric acid (glutaric acid:Co ratio of 0.16) or no polar organic compound). The catalysts were promoted with platinum to achieve a final composition of 42% Co-0.2% Re-0.03% Pt/TiO$_2$—SiO$_2$.

TABLE 10

| Step | Base (g) | Co(NO$_3$)$_2$ 6H$_2$O (g) Purity 98% | Co(NO$_3$)$_2$ 6H$_2$O (g) Purity 100% | Co$_3$O$_4$ (g) | Co (g) | Citic acid (g) | Perrhenic acid (g) | Re (g) | Solution volume (ml) | Calc wt (g) | % Co (approx.) |
|---|---|---|---|---|---|---|---|---|---|---|---|
| 1 | 20 | 26.53 | 26 | 7.17 | 5.26 | 3.75 | 0.0480 | 0.0231 | 26.6 | 27.2 | 19.4 |
| 2 |    | 26.53 | 26 | 7.17 | 5.26 | 3.75 | 0.0480 | 0.0231 | 25.8 | 34.4 | 30.6 |
| 3 |    | 26.53 | 26 | 7.17 | 5.26 | 3.75 | 0.0480 | 0.0231 | 26.1 | 41.6 | 38.0 |
| 4 |    | 26.53 | 26 | 7.17 | 5.26 | 3.75 | 0.0480 | 0.0231 | 24.2 | 48.8 | 43.2 |

Example 18

Preparation of Catalysts Using Titania-Modified Silica Support, Alkoxide Method (Reference)

Catalyst precursors having the composition 42% Co-0.2% Re-0.03% Pt/TiO$_2$—SiO$_2$ was made using the reagents in Table 11.

TABLE 11

| | Supplier | Code | Purity |
|---|---|---|---|
| Titanium(IV) isopropoxide | Sigma-Aldrich | 205273 | 97% |
| Cobalt nitrate hexahydrate | Alfa Aesar | — | 98% |
| Tetraammine platinum hydroxide | Alfa Aesar | 38201-97-7 | 9.3% Pt w/w |
| Silica | Grace Davison | (180-300 μm) | |
| Citric acid monohydrate (CA) | Sigma Aldrich | C1909 | ACS Reagent |
| Perrhenic acid | Sigma Aldrich | 65-70 wt % solution in water | 99.99% |

Example 19

Fischer-Tropsch Reaction Tests

The catalysts obtained in Examples 9, 10, 16 and 17 were tested for Fischer Tropsch synthesis (FTS) performance. The catalysts were diluted with SiC at a 1:18 ratio and then loaded in a fixed-bed combinatorial reactor (L/D 31 cm) and reduced using pure hydrogen at 400° C. for 120 minutes at Gas Hourly Space Velocity (GHSV)=15 000 per hour. The temperature was increased from room temperature to 400° C. at 1° C./min. After the reduction, the reactor was cooled to 165° C. and the gas was switched from hydrogen to synthesis gas. The operating conditions were kept constant for 1 hour. The pressure was then increased to 20 bar at the flow rate of the reaction and held for 1 hour. The temperature was then increased from 165° C. to 190° C. at a ramp rate of 4° C./hour, from 190 to 210° C. (GHSV=12 400 per hour) at 2° C./hour and then kept at 210° C. (GHSV=12 400 per hour) for about 120 hours. The Fischer Tropsch reaction was carried out for a total of 160 hours.

The deactivation rate of the catalyst was calculated via a linear regression analysis of the percent of CO converted during the reaction between a time on stream of 24 hours until the end of the run (160 hours).

The activity of the catalyst, in mol CO hr$^{-1}$ g$_{Co}$$^{-1}$, at 24 hours time on stream was calculated via $$\text{activity} = \frac{CO\ \%\ \text{conversion}}{100\%}.$$

$$\frac{CO\ \text{flow rate in}\ \frac{mL}{min} \cdot 60\ \frac{min}{hr}}{22400\ \frac{mL}{mol\ CO}} \cdot \frac{1}{\text{catalyst weight in g} \cdot 0.42}$$

The intrinsic activity, or turnover frequency (TOF) in mol CO converted per second, was calculated using:

$$TOF = \frac{\text{activity} \cdot 58.93\ g\frac{CO}{mol}}{\%\ \text{dispersion} \cdot DOR \cdot 3600}$$

The FTS performance of the catalysts made from the modified silica supports of Examples 1 and 5 and from a bare silica support of reference Example 17 and a reference titania-modified support (aqueous method) are shown in Table 12. The FTS performance of catalysts made from the titania-modified silica supports prepared by the alkoxide method of reference Example 18 are shown in Table 13.

The results show that catalysts made using the zirconia-modified supports and the chromium oxide-modified supports display particularly good FTS performance, comparable to a reference catalyst made using a titania-modified silica catalyst support.

Example 20

Comparison of Catalyst Porosity

The BET surface area of catalysts obtained in Examples 9, 16 and 17 was determined using nitrogen physisorption at 77 K in a Micromeritics Tristar II instrument. Prior to measurement, all samples were degassed in nitrogen at 100° C. for 3 hours. The pore size distribution, average pore size and total pore volume were determined using a DFT or BET calculation method. For the DFT method, with adsorption isotherm pressure points over the range 0.25-0.99 p/po, a Micromeritics built-in cylindrical model based on oxide surfaces was chosen, and a high degree of regularisation applied. For the BET method, the BJH pore size distribution was determined with 63 pressure data points, using the Halsey: Faas correction. In all cases, the reported average pore diameter is taken from adsorption measurements.

The average pore diameter of catalysts made from the modified silica supports of Examples 1 and 5 and from a reference bare silica support and a reference titania-modified support (aqueous method) are shown in Table 12. The average pore diameter of catalysts made from the reference titania-modified silica supports prepared by the alkoxide method of Example 18 are shown in Table 13.

Example 21

Comparison of $Co_3O_4$ Particle Size ($D_o$) of Catalysts

The diffraction patterns of fresh catalysts obtained in Example 9 (made from supports A2 and E) and fresh catalysts obtained using bare silica (Example 17), reference titania-modified supports using the aqueous method (Example 16) and reference titania-modified supports using the alkoxide method (Example 18) were collected on a fully automated Siemens D5000 theta/theta powder diffractometer using Cu Kα radiation at BegbrokeNano, Oxford University and compared. Each sample was ground thoroughly before loading into a spinner carousel in air. Data were collected over the range 10-80° 2θ, with a step size of 0.05° and a step length of 12 s. The average $Co_3O_4$ crystallite size ($D_O$), and the theoretical % dispersion of the $Co_3O_4$ crystallites were determined via the method hereinbefore described in relation to Example 14. The $Co^0$ metal size was estimated by multiplying the $Co_3O_4$ particle size by 75%.

The results for catalysts made from the modified silica supports of Examples 1 and 5 and from a reference bare silica support and a reference titania-modified support (aqueous method) are shown in Table 12. The results for catalysts made from the reference titania-modified silica supports prepared by the alkoxide method of Example 18 are shown in Table 13.

Example 22

Comparison of the Degree of Reduction (DOR)

TPR experiments were carried out using the Altamira AMI200 instrument. About 50 mg of the sample of catalyst (the catalysts of Example 9 (made from supports A2 and E) and catalysts obtained using bare silica (Example 17), reference titania-modified supports using the aqueous method (Example 16) and reference titania-modified supports using the alkoxide method (Example 18)) was loaded into a U-shaped quartz tube, with a small wad of quartz wool above and below the sample. The samples were first degassed in argon at 150° C. for 30 minutes, before decreasing the temperature to 50° C. and changing the flow to 5% $H_2$ in Ar. The temperature was then ramped to 800° C. at 5° C./min, and held for one hour, whilst the TCD signal was monitored. A moisture trap was not used. Quantification of the amount of hydrogen consumed was carried out by calibration of a 5% $H_2$ in Ar stream.

The reduction experiment was carried out using the same instrument using a fresh sample of catalyst. The samples were degassed in argon at 100° C. for 60 minutes. The flow was then changed to 5% $H_2$ in Ar and ramped to 400° C. at 2° C./min, and held for two hours, whilst the TCD signal was monitored. Calibration and quantification of the gas stream was carried out as above.

DOR was calculated by comparing the hydrogen consumed in two experiments using the following formula:

$$DOR = \frac{\text{mol } H_2/g\ \text{catalyst consumed up to } 400°\ C.}{\text{mol } H_2/g\ \text{catalyst consumed up to } 800°\ C.} \times 100\%$$

The results for catalysts made from the modified silica supports of Examples 1 and 5 and from a reference bare silica support (Example 17) and a reference titania-modified support (aqueous method, Example 16) are shown in Table 12. The results for various catalysts made from the reference titania-modified silica supports prepared by the alkoxide method of Example 18 are shown in Table 13.

TABLE 12

| Support used | % CO conversion | Δ % CO conversion (%/day) | Selectivity (%) $C_{5+}$ | Selectivity (%) $CH_4$ | Activity mol CO/hr/g Co | Run # | $D_0$ (nm) | Ave. pore size* (Å) | DOR (%) |
|---|---|---|---|---|---|---|---|---|---|
| 16% TiO$_2$ (reference Example 14) | 73.6 | −1.12 | 86.4 | 9.3 | 0.273 | 69 | 7.1(4) | 125.1 | 83.6 |
| Support A2 (22% ZrO$_2$, method A, calcined 250° C.) | 83.2 | −1.43 | 87.3 | 8.8 | 0.278 | 69 | 8.8(8) | 143.5 | 95.6 |
| Support E (15% Cr$_2$O$_3$, method A, dried 100° C.) | 71.3 | −2.22 | 85.0 | 10.1 | 0.238 | 69 | 4.7(9) | 127.2 | 67.0 |
| Bare SiO$_2$ (reference Example 15) | 78.9 | −1.63 | 87.8 | 8.2 | 0.352 | 46 | 5.1(2) | 169.6 | 77.6 |

*Pore size calculated by DFT method

TABLE 13

| Catalyst code | % CO conversion | Δ % CO conversion (%/day) | Selectivity (%) $C_{5+}$ | Selectivity (%) $CH_4$ | Activity mol CO/hr/g Co | Run # | $D_0$ (nm) | Ave. pore size* (Å) | DOR (%) |
|---|---|---|---|---|---|---|---|---|---|
| Citric acid, diluted lab-scale [1011-02-005-2] | 75.7 | −0.69 | 87.9 | 8.2 | 0.243 | 61 | 7.8(2) | 93.4 | 82.6 |
| Citric acid, standard lab-scale [1011-26-003-2] | 66.8 | −0.61 | 86.5 | 9.1 | 0.250 | 44 | 9.0(5) | 83.5 | 80.0 |
| Citric acid, 150 kg [1101-05-003-1] | 72.4 | −1.37 | 86.5 | 9.6 | 0.242 | 46 | 9.6(3) | 93.2 | 94.7 |
| Citric acid, labscale [1104-01-003-1] | 73.4 | −1.96 | 89.0 | 8.0 | 0.279 | 53 | 12.9(5) | — | 84.9 |
| No polar organic compound [1012-09-016-2] | 73.6 | −1.11 | 87.1 | 8.7 | 0.280 | 46 | 10.8(9) | 101.7 | 87.2 |
| Citric acid, 100 kg [1108-26-003-1] | 73.9 | −0.91 | 88.2 | 8.5 | 0.273 | 61 | 10.6(9) | 93.6 | 88.2 |
| Acetic acid [1107-25-005-1] | 82.4 | −1.12 | 88.1 | 8.0 | 0.267 | 61 | 6.7(3) | 108.1 | 87.3 |
| Malic acid [1108-03-005-1] | 75.5 | −0.98 | 87.6 | 8.5 | 0.263 | 61 | 6.6(3) | 108.3 | 80.9 |
| Glutaric acid [1108-03-005-7] | 78.7 | −0.80 | 86.9 | 8.6 | 0.281 | 61 | 5.1(2) | 108.5 | 87.7 |

*Pore size calculated by BJH method

The FTS performance set of reference catalysts prepared on titania-modified silica (via the alkoxide method) is given in Table 15. The Co$_3$O$_4$ crystallite size of this set of catalysts has been varied through a selection of methods, e.g. dilution of the impregnation solution, use of a different organic fuel (polar organic compound). It is clear from this data that the FTS activity of the set of reference catalysts varies as the particle size varies, although all catalysts maintain a % CO conversion that is greater than 60%. As there is a significant difference in the degree of reduction (DOR) of the catalyst at standard conditions, this must be considered in determining the intrinsic activity of the cobalt sites. A plot of the turnover frequency of these catalysts against the average Co$_3$O$_4$ particle size is shown in FIG. 1. This data set has been fit with a linear trend line (r=0.978), showing that the intrinsic activity of the Co$^0$ site increases linearly as the particle size increases over this whole size range (estimated Co$^0$ size 3.8-9.7 nm).

The CH$_4$ selectivity of the set of reference titania-modified silica catalysts varies between 8.0 and 9.5% (the estimated error on the measurement is 0.5%). The apparent variation in CH$_4$ selectivity of this set of catalysts may be a factor of the concomitant variation in the % CO conversion, as the selectivities do not correlate to changes in the pore size or any other factor measured here. This suggests that the intrinsic selectivities of these catalysts may not be significantly different.

Figure 2:
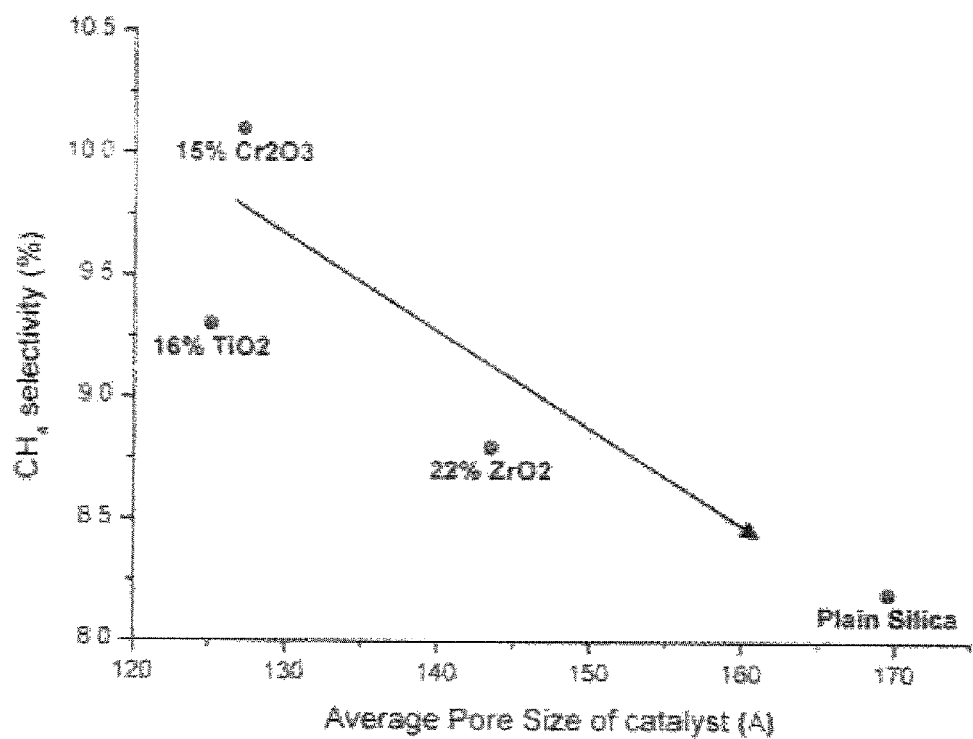
FIG. 2 shows variation in methane selectivity with average pore size of the catalyst.

The FTS performance of the catalysts made from the ZrO$_2$- and Cr$_2$O$_3$-modified supports shown in Table 14, along with the reference bare silica catalyst and reference titania-modified (aqueous method) catalyst show that silica modified with ZrO$_2$, Cr$_2$O$_3$ or TiO$_2$ via an aqueous method leads to a catalyst with CO conversion levels between 70 and 85%. Therefore, catalysts made from ZrO$_2$- and Cr$_2$O$_3$-modified supports have been shown to function well as Fischer-Tropsch catalysts. The catalyst supported on bare silica also has a conversion level in this range. However, a significant difference in the methane selectivities of these catalysts is observed. FIG. 2 shows the variation in methane selectivity with pore size for this set of catalysts and shows that CH$_4$ selectivity tends to increase as the average pore size decreases. FIG. 2 also shows that variations in methane selectivity appear not to be solely down to changes in pore size but is also affected by the catalyst support modifier. In particular, although chromium oxide-modified support catalysts and titanium oxide-modified support catalysts have similar pore size, they have a difference in methane selectivity of about 1%.

The results in Table 14 highlights that catalysts made from $ZrO_2$-modified supports are particularly advantageous as they perform well as a Fischer-Tropsch catalyst and have good $CH_4$ selectivity compared to reference catalyst based on titania-modified supports.

The invention claimed is:

1. A method for the preparation of a Fischer-Tropsch catalyst precursor comprising:
forming a modified catalyst support by the steps of:
a) treating a catalyst support material with an aqueous solution or dispersion comprising a metal source and one or more polar organic compounds, wherein the metal source comprises one or more of a zirconium metal source, a chromium metal source, a manganese metal source and an aluminium metal source; and
b) drying the treated support;
c) and optionally calcining the treated support; and
forming the Fischer-Tropsch catalyst precursor using the modified catalyst support by depositing a solution or suspension comprising at least one catalyst metal precursor and a complexing/reducing agent onto the modified catalyst support.

2. The method of claim 1, wherein the metal source comprises two or more different metals.

3. The method of claim 1, further comprising:
d) treating the modified catalyst support obtained in step b), or optionally obtained in step c), with a further aqueous solution or dispersion comprising a metal source and one or more polar organic compounds, wherein the metal source comprises a different metal to the metal in the metal source comprised in step a); and
e) drying the treated support of step d);
f) and optionally calcining the treated support.

4. The method of claim 3, wherein the metal source in the further aqueous solution or dispersion used in step d) comprises one or more of a zirconium metal source, a manganese metal source, a chromium metal source, an aluminium metal source or a titanium metal source.

5. The method of claim 1, wherein prior to step a) the catalyst support material undergoes steps comprising:
d) treating the catalyst support with a further aqueous solution or dispersion comprising a metal source and one or more polar organic compounds, wherein the metal source comprises a different metal to the metal in the metal source comprised in step a); and
e) drying the treated support of step d);
f) and optionally calcining the treated support.

6. The method of claim 1, wherein the method of treating is impregnating.

7. The method of claim 1, wherein the metal source in step a) comprises one or both of a zirconium metal source and a chromium metal source.

8. The method of claim 1, wherein the metal source in step a) comprises a zirconium metal source.

9. The method of claim 1, wherein the zirconium metal source in step a) is zirconium dinitrate oxide hydrate.

10. The method of claim 1, wherein the metal source in step a) comprises a chromium metal source.

11. The method of claim 10, wherein the chromium metal source in step a) is chromium (III) nitrate nonahydrate.

12. The method of claim 1, wherein the metal source in step a) comprises a manganese metal source.

13. The method of claim 12, wherein the manganese metal source is manganese (II) nitrate tetrahydrate.

14. The method of claim 1, wherein the metal source in step a) comprises an aluminium metal source.

15. The method of claim 14, wherein the aluminium metal source is aluminium nitrate.

16. The method of claim 1, wherein the polar organic compound in step a) is a carboxylic acid.

17. The method of claim 16, wherein the carboxylic acid is citric acid.

18. The method of claim 16, wherein the carboxylic acid is lactic acid.

19. The method of claim 1, wherein the polar organic compound in step d) is a carboxylic acid.

20. The method of claim 19, wherein the carboxylic acid is citric acid.

21. The method of claim 19, wherein the carboxylic acid is lactic acid.

22. The method of claim 1, wherein the catalyst support material is a refractory oxide.

23. The method of claim 22, wherein the refractory oxide is silica.

24. The method of claim 1, wherein the modified catalyst support is a modified Fischer-Tropsch catalyst support.

25. The method of claim 1, wherein forming the Fischer-Tropsch catalyst precursor further comprises:
optionally drying the modified catalyst support onto which the solution or suspension has been deposited; and
calcining the modified catalyst support onto which the solution or suspension has been deposited.

26. The method of claim 25, wherein the calcination is carried out in an oxygen-containing atmosphere.

27. A Fischer-Tropsch catalyst precursor produced in accordance with the method of claim 25.

28. A Fischer-Tropsch catalyst comprising the activated catalyst precursor of claim 27.

29. A method for conducting a Fischer-Tropsch reaction comprising catalyzing reactants in the presence of the Fischer-Tropsch catalyst of claim 28 to catalyse a Fischer-Tropsch reaction.

30. A method of conducting a Fischer Tropsch reaction comprising using the Fischer-Tropsch catalyst of claim 28 in a microchannel reactor, in which the performance of the catalyst is substantially maintained over a reaction period of about 5000 hours or more without regeneration of the catalyst, such that the contact time is less than 500 milliseconds, the CO conversion is greater than 50% and the methane selectivity is less than 15%.

31. The method of claim 30, wherein the CO conversion is greater than 60%.

32. The method of claim 30, wherein the methane selectivity is less than 10%.

33. The method of claim 30, wherein the reaction period is about 8000 hours or more.

34. The method of claim 30, wherein the microchannel reactor comprises one or more heat exchange channels adjacent to and/or in thermal contact with one or more process microchannels.

35. The method of claim 30, wherein the microchannel reactor is capable of high heat flux for cooling of process microchannels during the Fischer Tropsch reaction such that the temperature of a reactant composition at the entrance to the process microchannels is within about 200° C. of the temperature of a product at the exit of the process microchannels.

36. A method of conducting a Fischer Tropsch reaction comprising using the Fischer-Tropsch catalyst of claim 28 in a microchannel reactor in a temperature range of from about 180° C. to about 230° C., in which the deactivation rate of the catalyst measured as percent loss of CO conversion per day is 0.09% or less over a reaction period of about 5000 hours or more.

37. A method of conducting a Fischer Tropsch reaction comprising using a catalyst derived from the Fischer-Tropsch catalyst precursor according to claim 27 in a microchannel reactor, in which the performance of the catalyst is substantially maintained over a reaction period of about 5000 hours or more without regeneration of the catalyst, such that the contact time is less than 500 milliseconds, the CO conversion is greater than 50% and the methane selectivity is less than 15%.

38. A method of conducting a Fischer Tropsch reaction comprising using a catalyst derived from the Fischer-Tropsch catalyst precursor according to claim 27 in a microchannel reactor in a temperature range of from about 180° C. to about 230° C., in which the deactivation rate of the catalyst measured as percent loss of CO conversion per day is 0.09% or less over a reaction period of about 5000 hours or more.

39. The method of claim 1, wherein the complexing/reducing agent comprises one or more carboxylic acids.

40. The method of claim 1, wherein the catalyst metal precursor is a cobalt-containing precursor.

41. The method of claim 40, wherein the cobalt-containing precursor is cobalt nitrate.

42. The method of claim 1, wherein the catalyst metal precursor comprises cobalt nitrate.

43. The method of claim 1, wherein the formed Fischer-Tropsch catalyst precursor comprises at least 35 wt % Co.

44. The method of claim 43, wherein the at least 35 wt % Co is at least partially in the form of $Co_3O_4$.

45. The method of claim 44, wherein the numerical average particle diameter of the $Co_3O_4$ is 8 nm to 10 nm.

* * * * *